US006682905B1

(12) United States Patent
Schlessinger et al.

(10) Patent No.: US 6,682,905 B1
(45) Date of Patent: Jan. 27, 2004

(54) RECEPTOR-TYPE PHOSPHOTYROSINE PHOSPHATASE-ALPHA

(75) Inventors: Joseph Schlessinger, New York, NY (US); Jan M Sap, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/280,597

(22) Filed: Mar. 29, 1999

Related U.S. Application Data

(60) Division of application No. 08/448,288, filed on May 23, 1995, now Pat. No. 5,888,794, which is a division of application No. 08/015,985, filed on Feb. 10, 1993, now Pat. No. 5,538,886, which is a continuation-in-part of application No. 07/654,188, filed on Feb. 26, 1991, now abandoned, which is a continuation-in-part of application No. 07/551,270, filed on Jul. 11, 1990, now abandoned.

(51) Int. Cl.$^7$ .............................. C12Q 1/42; C12N 9/16; C12N 15/55

(52) U.S. Cl. ........................ 435/21; 435/196; 536/23.2

(58) Field of Search .................... 435/21, 196; 536/23.2

(56) References Cited

FOREIGN PATENT DOCUMENTS

| WO | WO 92/01050 | 1/1992 |
|---|---|---|
| WO | WO 94/01119 | 1/1994 |
| WO | WO 94/03610 A1 | 2/1994 |
| WO | WO 94/09037 A1 | 4/1994 |

OTHER PUBLICATIONS

Towbin, et al., "Electrophoretic Transfer of Proteins From Polyacrylamide Gels To Nitrocellulose Sheets: Procedure And Some Applications", Proc. Natl. Acad. Sci., vol. 76, No. 9, pp. 4350–4354, (1979).
Zheng, et al., "Cell Transformation and Activation of pp60$^{c-src}$ By Overexpression of a Protein Tyrosine Phophatase, Nature", vol. 359, No. 6393, pp. 336–339, (1992).
Church, et al., "Genomic Sequencing", Proc. Natl. Acad. Sci., vol. 81, pp. 1994–1995, (1984).
Kaplan et al., Cloning of three human tyrosine phosphatases reveals a multigene family of receptor–linked protein–tyrosine–phosphatases expressed in brain, Proc. Natl. Acad. Sci. USA 87: 7000–7004 (1990).
Sap et al., Cloning and expression of a widely expressed receptor tyrosine phosphatase, Proc. Natl. Acad. Sci. USA 87: 6112–6116 (1990).
Daum et al., Characterization of a human recombinant receptor–linked protein tyrosine phosphatase, J. Biol. Chem., 266: 12211–12215 (1991).
Gebbink et al., Cloning, expression and chromosomal localization of a new putative receptor–like protein tyrosine phosphatase, FEBS Lett. 290: 123–130 (1991).

Tsai et al., Isolation and characterization of temperature–sensitive and thermostable mutants of the human receptor–like protein tyrosine phosphatase LAR, J. Biol. Chem. 266(16): 10534–10543 (1991).
George and Parker, Preliminary characterization of phosphotyrosine phosphatase activities in human peripheral blood lymphocytes: Identification of CD45 as a phosphotyrosine phosphatase, J. Cell Biochem. 42: 71–81 (1990).
Jirik et al., Cloning of a novel receptor–linked protein tyrosine phosphatase from a human hepatoblastoma cell line, FASEB J. 4A: 2082 (Abstr. 2253) (1990).
Jirik et al., Cloning and chromosomal assignment of a widely expressed human receptor–like protein–tyrosine phosphatase, FEBS Lett. 273: 239–242 (1990).
Krueger et al., Structural diversity and evolution of human receptor–like protein tyrosine phosphatases, EMBO J. 9: 3241–3252 (1990).
Matthews et al., Identification of an additional member of the protein–tyrosine–phosphatase family: Evidence for alternative splicing in the tryosine phosphatase domain, Proc. Natl. Acad. Sci. USA 87: 4444–4448 (1990).
Ohagi et al., Sequence of a cDNA encoding human LRP (leukocyte common antigen–related peptide), Nucl. Acids Res. 18: 7159 (1990).
Streuli et al., Distinct functional roles of the two intracellular phosphatase like domains of the receptor–linked protein tyrosine phosphatases LCA and LAR, EMBO Journal 9: 2399–2407 (1990).
Kiener and Mittler, CD45–protein tyrosine phosphatase cross–linking inhibits T–cell receptor CD3–mediated activation in human T–cells, J. Immunol. 143: 23–28 (1989).
Mustelin et al., Rapid activation of the T–cell tyrosine protein kinase pp56lck by the CD45 phosphotyrosine phosphatase, Proc. Natl. Acad. Sci. USA 86: 6302–6306 (1989).
Ostergaard et al., Expression of CD45 alters phosphorylation of the lck–encoded tyrosine protein kinase in murine lymphoma T–cell lines, Proc. Natl. Acad. Sci. USA 86: 8959–8963 (1989).
Hall et al., Complete exon–intron organization of the human leukocyte common antigen (CD45) gene, J. Immunol. 141: 2781–2787 (1988).

(List continued on next page.)

*Primary Examiner*—Rebecca E. Prouty
(74) *Attorney, Agent, or Firm*—Beth A. Burrous; Foley & Lardner

(57) ABSTRACT

A novel receptor-type protein tyrosine phosphatase (RPTP) protein or glycoprotein and the DNA coding therefor is expressed in a wide variety of mammalian tissues. Included in this family of proteins are human RPTPα, human RPTPβ and human RPTPγ. The RPTP protein or glycoprotein may be produced by recombinant means. Antibodies to the proteins, methods for measuring the quantity of the proteins, methods for screening compounds, such as drugs, which can bind to the proteins and inhibit or stimulate their activity, are provided.

10 Claims, 16 Drawing Sheets

OTHER PUBLICATIONS

Figure 2:
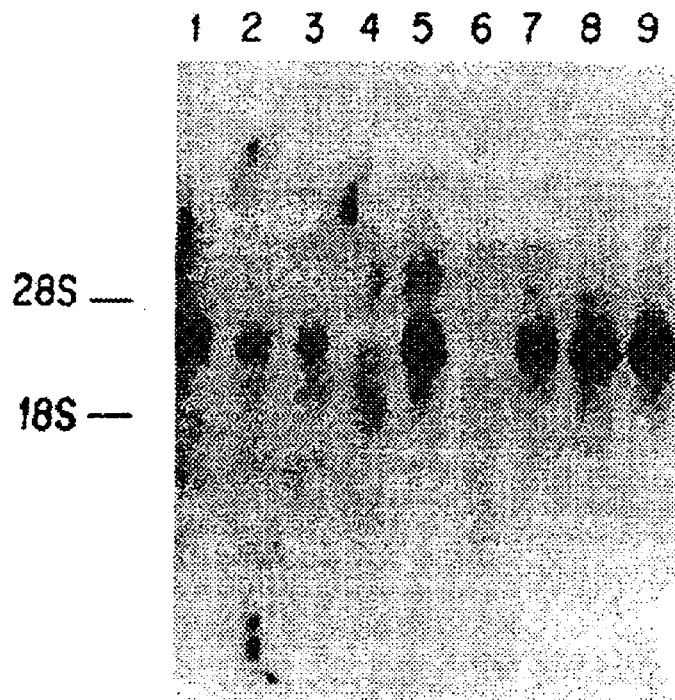

Streuli et al., A new member of the immunoglobulin superfamily that has a cytoplasmic region homologous to the leukocyte common antigen, J. Exp. Med. 168: 1523–1530 (1988).

Charbonneau et al., The leukocyte common antigen (CD45): A putative receptor–linked protein tyrosine phosphatase, Proc. Natl. Acad. Sci. USA 85: 7182–7186 (1988).

Ralph et al., Structural variants of human T200 glycoprotein (leukocyte–common antigen), EMBO J. 6: 1251–1257 (1987).

Streuli et al., Differential usage of three exons generates at least five different mRNAs encoding human leukocyte common antigens, J. Exp. Med. 166: 1548–1566 (1987).

Hariharan et al., Cloning and characterization of a receptor–class phosphotyrosine phosphatase gene expressed on central nervous system axons in Drosophila melanogaster, Proc. Natl. Acad. Sci. USA 88: 11266–11270 (1991).

Streuli et al., A family of receptor–linked protein tyrosine phosphatases in humans and Drosophila, Proc. Natl. Acad. Sci. USA 86: 8698–8702 (1989).

Gu et al., Identification, cloning, and expression of a cytosolic megakaryocyte protein–tyrosine–phosphatase with sequence homology to cytoskeletal protein 4.1, Proc. Natl. Acad. Sci. USA 88: 5867–5871 (1991).

Lombroso et al., Molecular characterization of a protein–tyrosine–phosphatase enriched in striatum, Proc. Natl. Acad. Sci. USA 88: 7242–7246 (1991).

Yang and Tonks, Isolation of a cDNA clone encoding a human protein–tyrosine phosphatase with homology to the cytoskeletal–associated proteins band 4.1, ezrin, and talin, Proc. Natl. Acad. Sci. USA 88: 5949–5953 (1991).

Chernoff et al., Cloning of a cDNA for a major human protein–tyrosine–phosphatase, Proc. Natl. Acad. Sci. USA, 87: 2735–2739 (1990).

Cool et al., Overexpression of a T–cell protein tyrosine phosphatase (PTPase) in BHK Cells, FASEB J. 4: A2078 (abstr. 2230) (1990).

Guan et al., Cloning and expression of a protein–tyrosine–phosphatase, Proc. Natl. Acad. Sci. USA 87: 1501–1505 (1990).

Thomas, et al., ABA, A novel member of the tyrosine phosphatase family, FASEB J. 4: A2078 (Abstr. 3140) (1990).

Tonks et al., CD45, an integral membrane protein tyrosine phosphatase, J. Biol. Chem. 265: 10674–10680 (1990).

Charbonneau et al., Human placenta protein–tyrosine–phosphatase: Amino acid sequence and relationship to a family of receptor–like proteins, Proc. Natl. Acad. Sci. USA 86: 5252–5256 (1989).

Cool et al., cDNA isolated from a human T–cell library encodes a member of the protein–tyrosine–phosphatase family, Proc. Natl. Acad. Sci. USA 86: 5257–5261 (1989).

Tonks et al., Purification of the major protein–tyrosine–phosphatases of human placenta, J. Biol. Chem. 263: 6722–6730 (1988).

Tonks et al., Demonstration that the leukocyte common antigen CD45 is a protein tyrosine phosphatase, Biochemistry 27: 8695–8701 (1988).

Matthews et al., Characterization of hemotopoietic intracellular protein tyrosine phosphatases: Description of a phosphatase containing an SH2 Domain and another enriched in proline–, glutamic acid–, serine–, and threonine–rich sequences, Molec. and Cell. Biol. 12: 2396–2405 (1992).

Plutzky et al., Isolation of a src homology 2–containing tyrosine phosphatase, Proc. Natl. Acad, Sci. USA 89: 1123–1127 (1992).

Yi et al., Protein tyrosine phosphatase containing SH2 domains: characterization, preferential expression in hematopoietic cells, and localization to human chromosome 12p12–p13, Mol. and Cell. Biol. 12: 836–846 (1992).

Shen et al., A protein–tyrosine phosphatase with sequence similarity to the SH2 domain of the protein–tyrosine kinases, Nature 352: 736–739 (1991).

Klarlund, Transformation of cells by an inhibitor of phosphatases acting on phosphotyrosine in proteins, Cell 41: 707–717 (1985).

Pallen et al., Purification of a phosphotyrosine phosphatase that dephosphorylates the epidermal growth factor receptor autophosphorylation sites, Ann. N.Y. Acad. Sci. 551: 299–308 (1988).

Butler et al., Characterization of a membrane–associated phosphotyrosyl protein phosphatase from the A431 human epidermoid carcinoma cell line, Eur. J. Biochem. 185: 475–483 (1989).

Cyert and Thorner, Putting it on and taking if off: Phosphoprotein phosphatase involvement in cell cycle regulation, Cell 57: 891–893 (1989).

Jones et al., Phosphotyrosyl–protein phosphatases, J. Biol. Chem. 264: 7747–7753 (1989).

Pingel and Thomas, Evidence that the leukocyte–common antigen is required for antigen–induced T lymphocyte proliferation, Cell 58: 1055–1065 (1989).

Pot and Dixon, A thousand and two protein tyrosine phosphatases, Biochem. Biophys. Acta. 1136: 35–43 (1992).

Fischer et al., Protein tyrosine phosphatases: A diverse family of intracellular and transmembrane enzymes, Science 253: 401–406 (1991).

Hunter, Protein–tyrosine phosphatases: The other side of the coin, Cell 58: 1013–1016 (1989).

Thomas, The leukocyte common antigen family, Ann. Rev. Immunol. 7: 339–369 (1989).

Tonks and Charbonneau, Protein tyrosine dephosphorylation and signal transduction, Trends in Biochem. Sci. 14: 497–500 (1989).

Berger et al., Guide to Molecular Cloning Techniques, Meth. Enzymol. 152: 393–399, 415–423, 432–447, 663–704 (1987).

Cannoll et al., "The Expression of a novel receptor–type tyrosine phosphatase suggests a role in morphogenesis and plasticity of the nervous system," *Development Brain Research*, Oct. 15, 1993, pp. 293–298, vol. 75, No. 2.

Carney et al., "Monoclonal antibody specific for an activated RAS protein," *Proc. Nat. Acad. Sci. USA*, Oct. 1986, pp. 7485–7489, vol. 83.

Guan et al., "Protein Tyrosine Phosphatase Activity of an Essential Virulence Determinant in Yersinia," *Science*, Aug. 3, 1990, pp. 553–556, vol. 249.

Krueger and Saito, "A human transmembrane protein–tyrosine–phosphatase, PTP, is expressed in brain and has an N–terminal receptor domain homologous to carbonic anhydrases," *Proc. Natl. Acad. Sci. USA*, 1992, pp. 7417–7421, vol. 89, No. 16.

Levy et al., "The cloning of a receptor–type protein tyrosine phosphatase expressed in the central nervous system," *Journal of Biological Chemistry*, May 15, 1993, pp. 10573–10581, vol. 268, No. 14.

Saiki et al., "Enzymatic amplification of β–globin genomic sequences and restriction site analysis for diagnosis of sickle cell anemia," *Science*, Dec. 20, 1985, pp. 1350–1354, vol. 230.

Scopes, *Protein Purification: Principles and Practice*, Springer–Verlag, New York, 1987 Table of Contents Only.

FIG.1A

```
                                850             870              890                910
                     tgtaccacttctggccaggtccccggcgcaccccaccggagtaccccaccctgcctgtggacaagctggagagggagattaaccg
                      V  P  L  L  A  R  S  P  S  T  N  R  K  Y  P  P  L  P  V  D  K  L  E  E  E  I  N  R
                         930             950              970                990             1010
                     gaggtggctgatgacaatcagctcttcagagaggaattcaacgctctccctgcttgtcctatccaggccacctgtgaggctgc
                      R  M  A  D  D  N  K  L  F  R  E  E  F  N  A  L  P  A  C  P  I  Q  A  T  C  E  A  A
                          1030            1050              1070             1090
                     ctccaaggaggaagaacaaggagaaaacaaagagctatgtaaacatcctgccctatgaccactctagagtgcacctgacacctgttg
                      S  K  E  E  N  K  E  [K  N  R  Y  V  N  I  L  P  Y  D  H  S  R  V  H  L  T  P  V  E
                          1110            1130              1150              1170
                      caggggtcccagattctgattacatcaacgcttcattcattaatggctaccaggaaagaaccaaattcatcgctgcacaaggac
                      G  V  P  D  S  D  Y  I  N  A  S  F  I  N  G  Y  Q  E  K  N  K  F  I  A  A  Q  G  P
                          1190            1210              1230             1250
                      cccagagaacgtgaatgactcttgggagaatgatgtggaaccaaaacacagctactattgtcatggtgaccaacctgaagg
                      K  E  E  T  V  N  D  F  W  R  M  I  W  E  Q  N  T  A  T  I  V  M  V  T  N  L  K  E
                          1270            1290              1310             1330
                      agagaagggtgtaaatgtgcccaatgctacacacgtacggacgggattctgatccagcaggtgggatgtccgtgtgtctgtcgaggatg
                      R  K  E  C  K  C  A  Q  Y  W  P  D  Q  G  C  W  T  Y  G  N  V  R  V  S  V  E  D  V
                          1350            1370              1390             1410             1430
                      tgctgttctcgtggactacacccagttcacccagctggccagagacttcgggtgccttcccccaattggagtcctcaaggaggtgaag
                      T  V  L  V  D  Y  T  V  R  K  F  S  I  Q  Q  V  G  D  V  T  N  R  K  P  Q  R  L  I
                          1450            1470              1490             1510
                      cctcagttcctccacttcaccagctggccagagggtgtgccagttcttcaccccattggggatgctgaagttcctcaagaagttgaag
                      T  Q  F  H  F  T  S  W  P  D  F  G  V  P  F  T  P  I  G  M  L  K  F  L  K  K  V  K
                          1530            1550              1570             1590
                      gctgtaaccctcagtacgcaggggctatcgtggtccactgtagtgcagtgcaggtgtagggcgactggcacctttgttgtcatcgatg
                      A  C  N  P  Q  Y  A  G  A  I  V  V  H  C  S  A  G  V  G  R  T  G  T  F  V  V  I  D  A
```

FIG.1B

```
      1610                1630                1650                1670
ccatgctggacatgatgcattcggagcgcaaagtggatgtatatgggtttgtgagccgatccgggcccagccgagctgccagatgta
  M  L  D  M  M  H  S  E  R  K  V  D  V  Y  G  F  V  S  R  I  R  A  Q  R  C  Q  M  V
        1690                1710                1730                1750               1770
cagacagacatgcagtacgtcttctctatataccaggccttctggagcattatctgtatgggaccacgaactggaagtggacttctc
  Q  T  D  M  Q  Y  V  F  I  Y] Q  A  L  L  E  H  Y  L  Y  G  D  T  E  L  E  V  T  S  L
         1790                1810                1830                1850
 ↓tagaaccccctacaaaaatttataacaagatccaggactagcaacggttagaggaggagtttaagaaattaacttc
   E  T  H  L  Q  K  I  Y  N  K  I  P  G  T  S  N  N  G  L  E  E  F  K  K  L  T  S
       1870                1890                1910                1930
aatcaaatccagaatgacaagatgcagagatcaaacgaggcgaagaagccacagacatgtgaacgcatcctcattgatgatcattccatat
  I  K  I  Q  N  D  K  M  R  T  G  N  L  P  A  N  M  K [ K  N  R  R  V  L  Q  I  I  P  Y
    1950                1970                1990                2010
gaattaacagagtgatcattccagtcaaacgaggcccctcttctccacacgttgggacttctggccatgatctggggtggaagtcctg
  E  F  N  R  V  I  I  P  V  K  R  G  E  E  N  T  D  Y  V  N  A  S  F  I  D  G  Y  R  Q
     2030                2050                2070                2090                2110
agaaagcttcctacattgccagccaggcccctcttctccacacgttgggacttctggccatgatctggggtggaagtcctg
  K  D  S  Y  I  A  S  Q  G  P  L  L  H  T  I  E  D  F  W  R  M  I  W  E  W  K  S  C
          2130                2150                2170                2190
ttctatcgtaatgctgctgacagaactggaagagagagggcaggagaggtgtgccagatgctggccatctgatgcctgcttgtctcctac
  S  I  V  M  L  T  E  L  E  E  R  G  Q  E  K  C  A  Q  Y  W  P  S  D  G  L  V  S  Y
       2210                2230                2250                2270
ggagacatcacagttgagctgaagctgaagaaggaggaggaatgtgaaagctacactgtccgagacctcctggtcaccaaccaggagag
  G  D  I  T  V  E  L  K  K  E  E  E  C  E  S  Y  T  V  R  D  L  L  V  T  N  T  R  E  N
```

FIG. 1C

```
                2290                    2310                    2330                    2350
            acaagagtcggcaaatccggccagttccacttccacggctgcctgaggtgggcatcccagcgacggcaaggcgtgatcaacat
             K  S  R  Q  I  R  Q  F  H  F  H  G  W  P  E  V  G  I  P  S  D  G  K  G  M  I  N  I
                2370                    2390                    2410                    2430                    2450
            cattgcagcagtgcagaagcagcagcagcagtcggggaaccatccatcactgtgctgcagtgccggggagaggacggacagga
             I  A  A  V  Q  K  Q  Q  Q  S  G  N  H  P  I  T  V  H  C  S  A  G  A  G  R  T  G
                2470                    2490                    2510                    2530
            acctctgtgccttgacacagtcctggacgtgaagcgaagtgaagggaattttagatgtcttccaactgtcaggagctgcggc
             T  F  C  A  L  S  T  V  L  E  R  V  K  A  E  G  I  L  D  V  F  Q  T  V  K  S  L  R  L
                2550                    2570                    2590                    2610
            tgcagagggccacacatggtccagacacatgaattctgctacaaggtggtacaggaatacattgacgccttttcaga
             Q  R  P  H  M  V  Q  T  L  E  Q  Y  E  F  C  Y[J]K  V  V  Q  E  Y  I  D  A  F  S  D
                2630                    2650                    2670                    2690
            ttatgccaacttcaagtgacaggtgacaggtgacaggcccacagacaggagaattgccttaatatttgtaatattctgtttttgttaat
             Y  A  N  F  K -.
                2710                    2730                    2750                    2770                    2790
            atacccaaaattgtatatatctttataactgtttaagaaatggcacataggcttctattacctgttagatgagagattttgtatgta
                2810                    2830                    2850                    2870
            aatgtgttagcactgataagtccttttccagtgttttattgggaattaatagtgtgatatttgggttgatatatgaattc
```

FIG. 1D

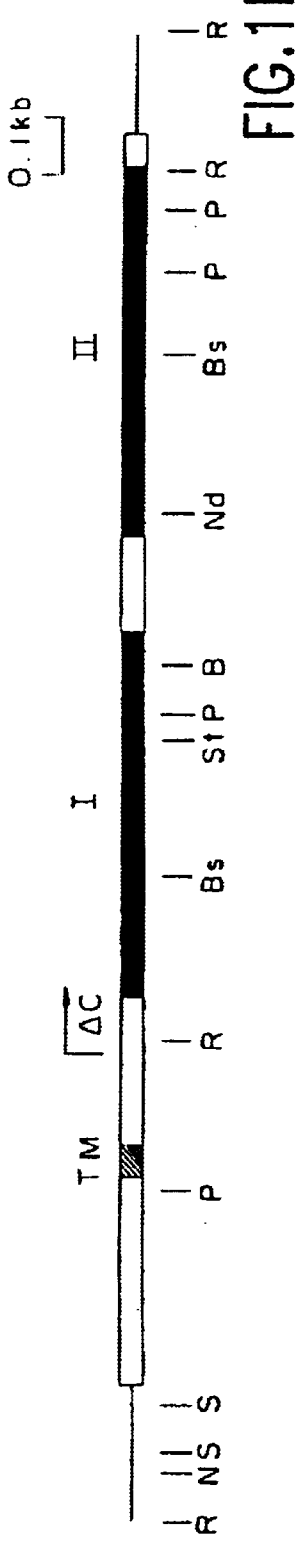

FIG. 1E

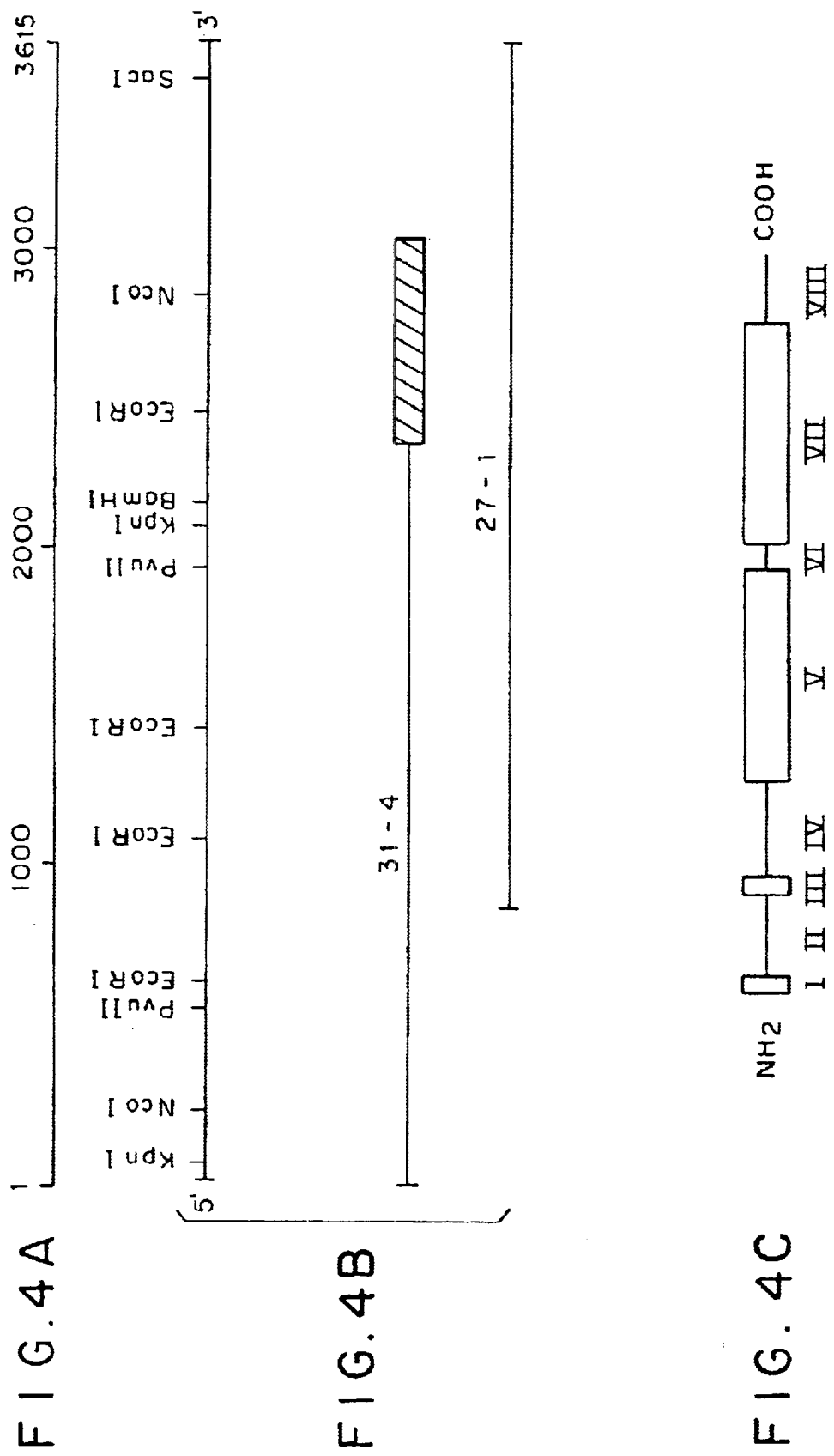
F I G. 4A
F I G. 4B
F I G. 4C

```
1  MDSWFILVLLGSGLICVS  ANNATTVAPSVGITRLINSSTAEPVKEEAKTSNPTSSLTSLSVAPTFSP      68
2                     F H         SLT   KT TLA N   S     VI                   68
1  NIILGPTYLITVNSSDSDNGTTRTASTNSIGITISPNGIWLPDNQFTDARTEPWEGNSSTAATTPETFP      136
2       L E V    H    R A  EGT    S   IE  I                                   136

1  PSGNSDSKDRRDETPIIAVMVALSSLLVLVFIIIVLYMI RFKKYKYKQAGSHSNSFRLSNGRTEDVEPQS    204
2                  A─────────────────────                                     195
1  VPLLARSPSTNRKYPPLPVDKLEEEINRRMADDNKLFREEFNALPACPIQATCEAASKEENKEKNRYV       272
2                                                                             263
1  NILPYDHSRVHLTPVEGVPDSDYINASFINGYQEKNKFIAAQGPKEETVNDFWRMIWEQNTATIVMVT       340
2                         A─                              V                   331
1  NLKERKECKCAQYWPDQGCWTYGNIRVSVEDVTVLVDYTVRKFCIQQVGDMTNRKPQRLITQFHFTSW       408
2                                        V        S    V                      399
1  PDFGVPFTPIGMLKFLKKVKACNPQYAGAIVVHCSAGVGRTGTFVVIDAMLDMMHTERKVDVYGFVSR       476
2                                                          S                  467
1  IRAQRCQMVQTDMQYVFIYQALLEHYLYGDTELEVTSLETHLQKIYNKIPGTSNNGLEEFKKLTSIK        544
2                                                                             535
1  IQNDKMRTGNLPANMKKNRVLQIIPYEFNRVIIPVKRGEENTDYVNASFIDGYRQKDSYIASQGPLLH       612
2                                                                             603
1  TIEDFWRMIWEWKSCSIVMLTELEERGQEKCAQYWPSDGLVSYGDITVELKKEEECESYTVRDLLVTN       680
2                                                                             671
1  TRENKSRQIRQFHFHCWPEVGIPSDGKGMISIIAAVQKQQQQSGNHPITVHCSAGAGRTGTFCALSTV       748
2                                              N                              739
1  LERVKAEGILDVFQTVKSLRLQRPHMVQTLEQYEFCYKVVQEYIDAFSDYANFK                     802
2                                                                             793
```

FIG. 4D

```
              10         20         30         40
LCA      NqnKNRYVdILPYDynRVeL  sEinGdagSnYINASyldGfkEprKyIAA
         | ||||| |||||  ||     |   | |||||  |  |   | |||
RPTPase α NKeKNRYVNILPYDHSRVhLtpvE  GvpdSDYINASfInGYqEknKfIAA
         | |||| ||                    |||||   ||
RPTPase β NKHKNRYINIvAYDHSRVKLaqLaeKDgKItDYINANYVDGYNrpKAYIAA
         |||||||||| |||||||| |  | ||  |||||||||||||    |||||
RPTPase γ NKHKNRYINIIAYDHSRVKLrpLpgKDsKhsDYINANYVDGYNkaKAYIAt CON      NkhKNRY-nII-YDhsRVkL—I—k—k-sdYINA-y-dGynepk-yIAa 50         60         70         80         90
LCA      QGPrdETVdDFWRMIWEQkatvIVMVTrceEgnrnKCAeYWPsMeegTra
         |||   |||  |||||||||     ||||    |    ||| ||       |
RPTPase α QGPkeETVnDFWRMIWEQNtatIVMVTNLkErkecKCAQYWPdqGewTYG
         |||  |  ||||||||||  |  ||| ||| |      ||  ||||  |  ||
RPTPase β QGPLKSTaEDFWRMIWEhNvevIVMITNLVEKGRRKCDQYWPadGSEEYG
         ||||||| ||||||||| |    |||||||||||||||||||||   |||||
RPTPase γ QGPLKSTfEDFWRMIWEqNtgiIVMITNLVEKGRRKCDQYWPtenSEEYG CON      QGPIk-TveDFWRMIWEqnt-vIVM-TnIvEkgrrKC-qYWP—gse-yg 100        110        120            130
LCA      fgdVvVkinqhkrcpDYiiqKI    nIvn    kkekatgRevThiq
         | |  |         |   |       |        |  |    |
RPTPase α NirVsVedVtVLv  DYTVRKFc    IqqvGd   mtnRkpqRIiTQfH
         | |   ||       ||||  |    |   |     |   |   |  ||
RPTPase β NfIVTqKSVqVLA  yYTVRnFtIRNTKIKK Gs  qKGRpsgRVVTQYH
         |  | ||    |   ||||||  ||||| | |     |||   |||  |||
RPTPase γ NiiVTIKStkihAc YTVRrFsiRNTKvKK GqkgnpKGRqneRVViQYH CON      ni-Vtvk-v-vIa—dYtvrkf—rntki-k-g-k—-kgr—-gRvvtqyh
```

FIG.5A

```
              140       150       160       170       180       190
LCA        FTSWPDhGVPedPhIILKIrrrVnAfsnffsGpIVVHCSAGVGRTGTyigID
           |||||  |||    |    ||       ||    |  ||||||||||||||   ||
RPTPase α  FTSWPDfGVPftPigmLKFIkKVkAcnpqyoGoIVVHCSAGVGRTGTfvVID
            |  |||  |||       |||    ||    |      |||||||||||||   ||
RPTPase β  YTQWPDMGVPEYsLPVLTFVRKooyAkrhovGPVVVHCSAGVGRTGTYIVID
           ||||||||||| ||||||||    |        | |  ||||||||||||||| |
RPTPase γ  YTQWPDMGVPEYoLPVLTFVRrssoArmpetGPVIVHCSAGVGRTGTYIViD CON        -T-WPDmGVPeyplpvL-fvr-v-oo------Gp-vVHCSAGVGRTGTyiviD 200       210       220       230
LCA        AMLegleoEnKVDVYGyVvkIRrQRCIMVQveoQYiIIhQALvE
           |||      |  ||||||| |   |||  |||   ||   |  |||  |
RPTPase α  AMLdmmhtErKVDVYGFVsrIRoQRCqMVQTdmQYVFIyQALIE
            ||      |   |    ||   || ||   |||    ||||||          ||
RPTPase β  SMLQQIqhEgTVNiIGFLKHIRsQRNYLVQTEEQYVFIHDtLvE
           ||||||    |||  |||||||| |||||||||||| ||||  ||
RPTPase γ  SMLQQIkdksTVNvIGFLKHIRtQRNYLVQTEEQYiFIHDoLIE CON        -MLqqi—e—V-vyGf-khiR-QR-y-VQteeQY-fIh-oL-E
```

FIG. 5B

```
              10              20              30              40
LCA      NksKNRnsnviPYdyNRVplkhelemskesehdsdessdddsdsEEpskY
           |||    |||  |||                              ||   |
RPTPase α  NmkKNRvlqlIPYEfNRViIpvkr                    GEEnTDY
           |||    ||||  |||                             ||  |||
RPTPase β  NrEKNRlSSlIPvERsRVGlssLs                     GE GTDY
           | ||||| ||  | || |||   |                     |  ||||
RPTPase γ  NkEKNRnSSvvPsERaRVGlapLp                     GmkGTDY CON        NkeKNRnss-iPyernRVg---l---------------------geegtdY 50              60              70              80              90
LCA      iNASFImsYwkpevmlAaQGPLkeTlgDFWqMlfqrKvkvlVMLTELkhg
         |||||  |    ||  || ||||  || |||  |       |||||||
RPTPase α vNASFIdCYrQkdsylAsQGPLLHTleDFWRMlWewKscsIVMLTELeer
         ||| | ||  |    |  | |||||| ||||||| ||
RPTPase β lNASYlMGYYQSNEFllTQHPLLHTlKDFWRMlWDHNAQlVVMlPDgQnm
         |||||||||| |||||||||||||| || |||||||||||| || |
RPTPase γ lNASYlMGYYrSNEFllTQHPLpHTtKDFWRMlWDHNAQllVMlPDnQsl CON      iNAS-lmgYyqsnefl-tQ-PLlhTikDFWrMlwdh-naqiVMl----q--

100             110             120             130             140
LCA      dQEiCAQYW geCkqlYGDleVdLKdldksstYTl RvfelrhskrkdSRtv
         || |||||| |   || ||||  || | ||     ||   |           ||
RPTPase α gQEkCAQYWPsdGlvsYGDltVeLKkeeeCESYTV RdllvtntreNkSRql
         ||  |||                              |         |       |
RPTPase β A EDEFVYWPn     kDEpi     NCESFkVTLmaeehkCLSNEEkll
         | ||||||||        |        ||| | |||    |||||| |
RPTPase γ A EDEFVYWPs     reEsm     NCEafLVTLiskdrlCLSNEEqil CON      aE-e--qYWps-g----ygd--v-lk---nces-lvt----e-r-clsne-r-i 150                     160             170             180
LCA      yQy              qY   tnWsveqlP aepKellSmlqvVkQKlpQk
         |                                | | | ||| |  ||    |
RPTPase α rQf              HF   hgWPevglP SdgKgmlSiloaV Qk   Qq
         |                                ||   |  ||     |||
RPTPase β lQDFlLEATQDDYVLEVRHFQCPKWPNPDsPlSkTFELlSVl              K
         ||||||||||||||||||||||||||||| |  | ||||| ||              |
RPTPase γ lhDFlLEATQDDYVLEVRHFQCPKWPNPDaPlSsTFELlnVl              K CON      iqdfileatqddyvlevrhfqcpkWpnpd-Pis-t-ellsvl------qk
```

FIG. 5C

```
              190       200       210       220       230
LCA      nsseGNkhhkslPIIiHCrdGsqqTGiFCALInILEsaetEevvDiFQvVKa
          ||    |   ||  |   || ||||  ||     |   | || ||
RPTPase α  qqsGNh    PitVHCsaGagrTGTFCALsTvLErvkaEgiIDVFQLVKs
          |      |   ||  |    ||||||| |         |    ||  |
RPTPase β  EEAaNR    DGPmIVHDEhGqVtAGTFCALTTLmhQLEkENsVDVyQVAKM
          ||| |     ||| |||||| | ||  ||||||  ||| || ||| |||||
RPTPase γ  EEAltR    DGPtIVHDEyGaVsAGmICALTTLsqQLEnENaVDVfQVAKM CON       -eea-nr----dgP-ivH-e-Gav---GtfCALttIleqle-En-vDvfQv-Km 240       250
LCA      LrkaRPgMVsTfEQYqFIYdVias
          |   || ||  |  |||  | |
RPTPase α  LaLqRPhMVqTIEQYeFcYKVvqe
          | ||       ||| |  |||
RPTPase β  INLMRPGVFaDIEQYQFIYKViLS
          ||||||||| ||||||| ||  ||
RPTPase γ  INLMRPGVFtDIEQYQFIYKarLS CON       -nlmRPg------iEQYqFIYkvils
```

FIG. 5D

```
  1 ATGGATTCCTGGTTCATTCTTGTTCTGCTCGGCAGTGGTCTGATATGTGTCAGTGCCAAC  60
  1 [M  D  S  W  F  I  L  V  L  L  G  S  G  L  I  C  V  S] A  N   20
       SIGNAL PEPTIDE

61 AATGCTACCACAGTTGCACCTTCTGTAGGAATTACAAGATTAATTAACTCATCAACGGCA 120
 21 N  A  T  T  V  A  P  S  V  G  I  T  R  L  I  N  S  S  T  A   40

121 GAACCAGTTAAAGAAGAGGCCAAAACTTCAAATCCAACTTCTTCACTAACTTCTCTTTCT 180
 41 E  P  V  K  E  E  A  K  T  S  N  P  T  S  S  L  T  S  L  S   60

181 GTGGCACCAACATTCAGCCCAAATATAACTCTGGGACCCACCTATTTAACCACTGTCAAT 240
 61 V  A  P  T  F  S  P  N  I  T  L  G  P  T  Y  L  T  T  V  N   80

241 TCTTCAGACTCTGACAATGGGACCACAAGAACAGCAAGCACCAATTCTATAGGCATTACA 300
 81 S  S  D  S  D  N  G  T  T  R  T  A  S  T  N  S  I  G  I  T  100

301 ATTTCACCAAATGGAACGTGGCTTCCAGATAACCAGTTCACGGATGCCAGAACAGAACCC 360
101 I  S  P  N  G  T  W  L  P  D  N  Q  F  T  D  A  R  T  E  P  120

361 TGGGAGGGGAATTCCAGCACCGCAGCAACCACTCCAGAAACTTTCCCTCCTTCAGGTAAT 420
121 W  E  G  N  S  S  T  A  A  T  T  P  E  T  F  P  P  S  G  N  140

421 TCTGACTCGAAGGACAGAAGAGATGAGACACCAATTATTGCGGTGATGGTGGCCCTGTCC 480
141 S  D  S  K  D  R  R  D  E  T [P  I  I  A  V  M  V  A  L  S  160
                                  TRANSMEMBRANE SEGMENT

481 TCTCTGCTAGTGATCGTGTTTATTATCATAGTTTTGTACATGTTAAGGTTTAAGAAATAC 540
161 S  L  L  V  I  V  F  I  I  I  V  L  Y  M  L] R  F  K  K  Y  180

541 AAGCAAGCTGGGAGCCATTCCAATTCTTTCCGCTTATCCAACGGCCGCACTGAGGATGTG 600
181 K  Q  A  G  S  H  S  N  S  F  R  L  S  N  G  R  T  E  D  V  200

601 GAGCCCCAGAGTGTGCCACTTCTGGCCAGATCCCCAAGCACCAACAGGAAATACCCACCC 660
201 E  P  Q  S  V  P  L  L  A  R  S  P  S  T  N  R  K  Y  P  P  220

661 CTGCCCGTGGACAAGCTGGAAGAGGAAATTAACCGGAGAATGGCAGACGACAATAAGCTC 720
221 L  P  V  D  K  L  E  E  E  I  N  R  R  M  A  D  D  N  K  L  240

721 TTCAGGGAGGAATTCAACGCTCTCCCTGCATGTCCTATCCAGGCCACCTGTGAGGCTGCT 780
241 F  R  E  E  F  N  A  L  P  A  C  P  I  Q  A  T  C  E  A  A  260

781 TCCAAGGAGGAAAACAAGGAAAAAAATCGATATGTAAACATCTTGCCTTATGACCACTCT 840
261 S  K  E  E [N  K  E  K  N  R  Y  V  N  I  L  P  Y  D  H  S  280
              PTPase DOMAIN I
```

FIG.8A

```
841  AGAGTCCACCTGACACCGGTTGAAGGGGTTCCAGATTCTGATTACATCAATGCTTCATTC  900
281   R  V  H  L  T  P  V  E  G  V  P  D  S  D  Y  I  N  A  S  F   300

901  ATCAACGGTTACCAAGAAAAGAACAAATTCATTGCTGCACAAGGACCAAAAGAAGAAACG  960
301   I  N  G  Y  Q  E  K  N  K  F  I  A  A  Q  G  P  K  E  E  T   320

961  GTGAATGATTTCTGGCGGATGATCTGGGAACAAAACACAGCCACCATCGTCATGGTTACC 1020
321   V  N  D  F  W  R  M  I  W  E  Q  N  T  A  T  I  V  M  V  T   340

1021 AACCTGAAGGAGAGAAAGGAGTGCAAGTGCGCCCAGTACTGGCCAGACCAAGGCTGCTGG 1080
341   N  L  K  E  R  K  E  C  K  C  A  Q  Y  W  P  D  Q  G  C  W   360

1081 ACCTATGGGAATATTCGGGTGTCTGTAGAGGATGTGACTGTCCTGGTGGACTACACAGTA 1140
361   T  Y  G  N  I  R  V  S  V  E  D  V  T  V  L  V  D  Y  T  V   380

1141 CGGAAGTTCTGCATCCAGCAGGTGGGCGACATGACCAACAGAAAGCCACAGCGCCTCATC 1200
381   R  K  F  C  I  Q  Q  V  G  D  M  T  N  R  K  P  Q  R  L  I   400

1201 ACTCAGTTCCACTTTACCAGCTGGCCAGACTTTGGGGTGCCTTTTACCCCGATCGGCATG 1260
401   T  Q  F  H  F  T  S  W  P  D  F  G  V  P  F  T  P  I  G  M   420

1261 CTCAAGTTCCTCAAGAAGGTGAAGGCCTGTAACCCTCAGTATGCAGGGGCCATCGTGGTC 1320
421   L  K  F  L  K  K  V  K  A  C  N  P  Q  Y  A  G  A  I  V  V   440

1321 CACTGCAGTGCAGGTGTAGGGCGTACAGGTACCTTTGTCGTCATTGATGCCATGCTGGAC 1380
441   H  C  S  A  G  V  G  R  T  G  T  F  V  V  I  D  A  M  L  D   460

1381 ATGATGCATACAGAACGGAAGGTGGACGTGTATGGCTTTGTGAGCCGGATCCGGGCACAG 1440
461   M  M  H  T  E  R  K  V  D  V  Y  G  F  V  S  R  I  R  A  Q   480

1441 CGCTGCCAGATGGTGCAAACCGATATGCAGTATGTCTTCATATACCAAGCCCTTCTGGAG 1500
481   R  C  Q  M  V  Q  T  D  M  Q  Y  V  F  I  Y  Q  A  L  L  E]  500

1501 CATTATCTCTATGGAGATACAGAACTGGAAGTGACCTCTCTAGAAACCCACCTGCAGAAA 1560
501   H  Y  L  Y  G  D  T  E  L  E  V  T  S  L  E  T  H  L  Q  K   520

1561 ATTTACAACAAAATCCCAGGGACCAGCAACAATGGATTAGAGGAGGAGTTTAAGAAGTTA 1620
521   I  Y  N  K  I  P  G  T  S  N  N  G  L  E  E  E  F  K  K  L   540
```

FIG. 8B

```
1621 ACATCAATCAAAATCCAGAATGACAAGATGCGGACTGGAAACCTTCCAGCCAACATGAAG 1680
 541  T  S  I  K  I  Q  N  D  K  M  R  T  G  N  L  P  A [N  M  K   560
                                                          PTPase Domain II
1681 AAGAACCGTGTTTTACAGATCATTCCATATGAATTCAACAGAGTGATCATTCCAGTTAAG 1740
 561  K  N  R  V  L  Q  I  I  P  Y  E  F  N  R  V  I  I  P  V  K   580

1741 CGGGGCGAAGAGAATACAGACTATGTGAACGCATCCTTTATTGATGGCTACCGGCAGAAG 1800
 581  R  G  E  E  N  T  D  Y  V  N  A  S  F  I  D  G  Y  R  Q  K   600

1801 GACTCCTATATCGCCAGCCAGGGCCCTCTTCTCCACACAATTGAGGACTTCTGGCGAATG 1860
 601  D  S  Y  I  A  S  Q  G  P  L  L  H  T  I  E  D  F  W  R  M   620

1861 ATCTGGGAGTGGAAATCCTGCTCTATCGTGATGCTAACAGAACTGGAGGAGAGAGGCCAG 1920
 621  I  W  E  W  K  S  C  S  I  V  M  L  T  E  L  E  E  R  G  Q   640

1921 GAGAAGTGTGCCCAGTACTGGCCATCTGATGGACTGGTGTCCTATGGAGATATTACAGTG 1980
 641  E  K  C  A  Q  Y  W  P  S  D  G  L  V  S  Y  G  D  I  T  V   660

1981 GAACTGAAGAAGGAGGAGGAATGTGAGAGCTACACCGTCCGAGACCTCCTGGTCACCAAC 2040
 661  E  L  K  K  E  E  E  C  E  S  Y  T  V  R  D  L  L  V  T  N   680

2041 ACCAGGGAGAATAAGAGCCGGCAGATCCGGCAGTTCCACTTCCATGGCTGGCCTGAAGTG 2100
 681  T  R  E  N  K  S  R  Q  I  R  Q  F  H  F  H  G  W  P  E  V   700

2101 GGCATCCCCAGTGACGGAAAGGGCATGATCAGCATCATCGCCGCCGTGCAGAAGCAGCAG 2160
 701  G  I  P  S  D  G  K  G  M  I  S  I  I  A  A  V  Q  K  Q  Q   720

2161 CAGCAGTCAGGGAACCACCCCATCACCGTGCACTGCAGCGCCGGGGCAGGAAGGACGGGG 2220
 721  Q  Q  S  G  N  H  P  I  T  V  H  C  S  A  G  A  G  R  T  G   740

2221 ACCTTCTGTGCCCTGAGCACCGTCCTGGAGCGTGTGAAAGCAGAGGGGATTTTGGATGTC 2280
 741  T  F  C  A  L  S  T  V  L  E  R  V  K  A  E  G  I  L  D  V   760

2281 TTCCAGACTGTCAAGAGCCTGCGGCTACAGAGGCCACACATGGTCCAGACACTGGAACAG 2340
 761  F  Q  T  V  K  S  L  R  L  Q  R  P  H  M  V  Q  T  L  E  Q   780

2341 TATGAGTTCTGCTACAAGGTGGTGCAGGAGTATATTGATGCATTCTCAGATTATGCCAAC 2400
 781  Y  E  F  C  Y  K  V  V  Q  E] Y  I  D  A  F  S  D  Y  A  N   800

2401 TTCAAGTAA 2409
 801  F  K  *   803
```

FIG.8C

US 6,682,905 B1

RECEPTOR-TYPE PHOSPHOTYROSINE PHOSPHATASE-ALPHA

This is a division of application Ser. No. 08/448,288, filed May 23, 1995 now U.S. Pat. No. 5,888,794, which is a divisional application Ser. No. 08/015,985, filed Feb. 10, 1993, now U.S. Pat. No. 5,538,886, which is a continuation-in-part of application Ser. No. 07/654,188, filed Feb, 26, 1991 abandoned, which is a continuation-in-part of application Ser. No. 07/551,270, filed Jul. 11, 1990, abandoned, the entire contents of each of which is incorporated herein by reference in its entirety.

1. INTRODUCTION

The invention in the field of biochemistry and cell and molecular biology relates to novel receptor-type protein tyrosine phosphatase proteins or glycoproteins, termed RPTPα, RPTPβ and RPTPγ (also designated R-PTPase-α, β and γ), DNA coding therefor, methods for production and identification of the proteins, and methods for screening compounds capable of binding to and inhibiting or stimulating PTPase enzymatic activity.

2. BACKGROUND OF THE INVENTION

The identification of several growth factor receptors and retroviral oncogenes as tyrosine-specific protein kinases indicated that protein phosphorylation on tyrosine residues plays a key role in cellular growth control. This notion has recently received support by the observation that the level of tyrosine phosphorylation of enzymes thought to play an important role in signal transduction (such as phospholipase C) correlates with their increased activity upon growth factor stimulation, thus establishing a functional role for tyrosine phosphorylation (Ullrich, A., et al., Cell 61:203–212 (1990)).

The degree and pattern of phosphorylation of tyrosine residues on cellular proteins are regulated by the opposing activities of protein-tyrosine kinases (PTKases; ATP:protein-tyrosine O-phosphotransferase, EC 2.7.1.112) and protein-tyrosine-phosphatases (PTPases; protein-tyrosine-phosphate phosphohydrolase, EC 3.1.3.48). The structural characteristics and evolution of PTKases as well as their role in the regulation of cell growth have been reviewed (Hunter, T., et al., Annu. Rev. Biochem. 54:897–930 (1985); Ullrich, A., et al., supra).

2.1. PTKases

Tyrosine kinases comprise a discrete family of enzymes having common ancestry with, but major differences from, serine/threonine-specific protein kinases (Hanks, S. K. et al., (1988) Science 241, 42–52). The mechanisms leading to changes in activity of tyrosine kinases are best understood for receptor-type tyrosine kinases which have a transmembrane topology (Ullrich, A. et al., supra). With such kinases, the binding of specific ligands to the extracellular domain of these enzymes is thought to induce their oligomerization leading to an increase in tyrosine kinase activity and activation of the signal transduction pathways (Ullrich, A. et al., supra). The importance of this activity is supported by the knowledge that dysregulation of kinase activity through mutation or over-expression is a mechanism for oncogenic transformation (Hunter, T et al., supra; Ullrich, A. et al., 1990, supra).

2.2. PTPases

The protein phosphatases are composed of at least two separate and distinct families (Hunter, T. Cell, 58:1013–1016 (1989)), the protein serine/threonine phosphatases and the protein tyrosine phosphatases. This is in contrast to protein kinases, which show clear sequence similarity between serine/threonine-specific and tyrosine-specific enzymes.

There appear to be two varieties of PTPase molecules. The first group is comprised of small, soluble enzymes that contain a single conserved phosphatase catalytic domain, and include (1) placental PTPase 1B (Charbonneau, H. et al., Proc. Natl. Acad. Sci. 86:5252–5256 (1989); Chernoff, J. et al., Proc. Natl. Acad. Sci. USA 87:2735–2789 (1990)), (2) T-cell PTPase (Cool, D. E. et al., Proc. Natl. Acad. Sci. USA 86:5257–5261 (1989)), and (3) rat brain PTPase (Guan, K., et al., Proc. Natl. Acad. Sci. USA, 87:1501–1505 (1990).

The second group is made up of the more complex, receptor-linked PTPases, termed R-PTPases (or RPTPs), which are of high molecular weight and contain two tandemly repeated conserved domains separated by 56–57 amino acids. One example of RPTPs are the leukocyte common antigens (LCA) (Ralph, S. J., EMBO J., 6:1251–1257 (1987); Charbonneau, H., et al., Proc. Natl. Acad. Sci. USA, 85:7182–7186 (1988)). LCA, also known as CD45, T200 and Ly-5 (reviewed in Thomas, M. L., Ann. Rev. Immunol. 7:339–369 (1989)) comprises a group of membrane glycoproteins expressed exclusively in hemopoietic (except late erythroid) cells, derived from a common gene by alternative splicing events involving the amino terminus of the proteins. Whereas the precise function of CD45 is unknown, many studies have implicated these antigens in a number of processes, including the activity of cytotoxic T lymphocytes and natural killer cells, IL-2 receptor expression, B-cell differentiation, and T lymphocyte proliferation (Pingel, J. T. et al., Cell 58:1055–1065 (1989)).

Other examples of RPTPs are the LCA-related protein, LAR (Streuli, M., et al., J. Exp. Med., 168:1523–1530 (1988)), and the LAR-related Drosophila proteins DLAR and DPTP (Streuli, M., et al., Proc. Natl. Acad. Sci. USA, 86:8698–8702 (1989)). Jirik et al. screened a cDNA library derived from the human hepatoblastoma cell line, HepG2, with a probe encoding the two PTPase domains of LCA (FASEB J. 4:A2082 (1990), abstr. 2253) and discovered a cDNA clone encoding a new RPTP, named He-PTP. The HePTP gene appeared to be expressed in a variety of human and murine cell lines and tissues.

While we are beginning to understand more about the structure and diversity of the PTPases, much remains to be learned about their cellular functions. It has been suggested (Tonks, N. K., et al., Biochemistry, 27:8695–8701 (1988)) that the small, soluble PTPase enzymes may have a "housekeeping" function. On the other hand, the RPTPs would be expected to be more restricted in their activities because of their location in the cell membrane and their potential regulation by extracellular ligands. Regarding the role of LCA (CD45) in T cells, it was found that T cell clones deficient in the expression of LCA failed to proliferate when stimulated by a specific antigen or by cross-linking of CD3 (Pingel, J. T., et al., supra). PTPase cross-linking inhibits T cell receptor CD3-mediated activation in human T cells (Kiener, P. A. et al., J. Immunol. 143:23–28 (1989)). The PTPase activity of LCA plays a role in the activation of $pp56^{lck}$, a lymphocyte-specific PTKase (Mustelin, T., et al., Proc. Natl. Acad. Sci. USA, 86:6302–6306 (1989); Ostergaard, H. L., et al., Proc. Natl. Acad. Sci. USA, 86:8959–8963 (1989)). These authors hypothesized that the phosphatase activity of LCA activates $pp56^{lck}$ by dephosphorylation of a C-terminal tyrosine residue, which may, in turn, be related to T-cell activation.

Using site-directed mutagenesis to determine which of four conserved cysteines in LCA (two per phosphatase domain) was required for enzyme activity toward artificial substrates, Streuli et al. (1989, supra) found that only one cysteine residue (residue 177 of LCA phosphatase domain-1) of LCA was essential for activity, indicating that, most likely, only the first phosphatase domain has enzymatic activity. However, the possibility that the second domain can dephosphorylate a different substrate was not excluded. More recently, Streuli et. al. (*EMBO J.*, 9:2399–2407 (1990)) determined that the second conserved domain of LCA (and of LAR) lacked detectable phosphatase activity but sequences within the domain could influence substrate specificity.

In order to better understand and to be able to control phosphotyrosine metabolism, one must comprehend not only the role of kinase activity, but also the action of phosphatase enzymes as well. Elevation of cellular phosphotyrosine may occur through mechanisms not involving the activation of a tyrosine kinase itself. For instance, expression of the v-crk oncogene, though not a tyrosine kinase itself, induces the phosphorylation of tyrosine residues through a poorly understood mechanism (Mayer, B. J. et al. (1988) *Nature* 332, 272–275). Potentially, such an outcome could result from either mutation of the substrate or through a general decrease in cellular phosphatase activity, especially in view of the normally high turnover rate of cellular tyrosine-phosphate (Sefton, B. M. et al. (1980) *Cell* 20, 807–816). The latter possibility is suggested by the demonstration that tyrosine phosphatase inhibitors can "reversibly transform" cells (Klarlund, J. K. *Cell* 41: 707–717 (1985)). PTPases could therefore be viewed as potential recessive oncogenes.

It is becoming clear that dephosphorylation of tyrosine can by itself function as an important regulatory mechanism. Dephosphorylation of a C-terminal tyrosine residue stimulates tyrosine kinase activity in the src-family of tyrosine kinases (Hunter, T. (1987) *Cell* 49, 1–4). Tyrosine dephosphorylation has been suggested to be an obligatory step in the mitotic activation of the MPF (maturation promoting factor) kinase (Morla, A. O. et al. (1989) *Cell* 58, 193–203). Lastly, mutant analysis of primitive eukaryotes has established crucial roles for serine phosphatase in cellular physiology (Cyert, M. S. et al. (1989) *Cell* 57, 891–893). These observations point out the need in the art for increasing our understanding of the mechanisms that regulate tyrosine phosphatase activity.

It is clear in the art that further analysis of structure-function relationships among these membrane receptors are needed to gain important understanding of the mechanisms of cell growth, differentiation, and oncogenesis.

3. SUMMARY OF THE INVENTION

The inventors have conceived of a role for RPTPs in cellular control mechanisms, both as potential anti-oncogenes, and as effectors in a newly discovered mechanism of transmembrane signalling. They therefore undertook a search for an RPTP potentially involved in such processes, and describe herein the identification of a novel, widely expressed member of the RPTP family, which has a transmembrane topology. Importantly, its extracellular domain is unrelated to any other RPTP heretofore described. The novel RPTPs, in a manner analogous to receptor tyrosine kinases, are subject to direct regulation by a variety of different extracellular ligands.

The present invention thus provides a human receptor-type protein tyrosine phosphatase (RPTP) protein or glycoprotein molecule other than leucocyte common antigen (LCA or CD45) and leucocyte common antigen-related protein (LAR), a functional derivative of the human RPTP or a homolog of the human RPTP in another mammalian species. When the molecule is of natural origin, it is substantially free of other proteins or glycoproteins with which it is natively associated. This naturally-occurring molecule is normally present in mammalian liver, kidney and brain. Alternatively, the RPTP molecule may not be of natural origin, such as one prepared by chemical or recombinant means.

The substantially pure RPTP protein or glycoprotein of the invention may be produced by biochemical purification of the glycoprotein of natural origin; alternatively, the RPTP may be produced by recombinant means in prokaryotic or eukaryotic hosts.

In particular, the invention is directed to the molecule RPTPα, preferably human RPTPα having the amino acid sequence (SEQ ID NO:1) shown in FIGS. 4 and 8, or a functional derivative thereof. In another embodiment, the invention is directed to human RPTPβ. In yet another embodiment, the invention is directed to human RPTPγ.

The invention is further directed to a nucleic acid molecule consisting essentially of a nucleotide sequence encoding RPTPα of mouse or human origin, or RPTPβ or RPTPγ, both of human origin, or a functional derivative thereof. The nucleic acid molecule may be in the form of cDNA or genomic DNA. Preferably, the nucleic acid molecule has the nucleotide sequence of human RPTPα-encoding DNA, SEQ ID NO:2, also shown in FIG. 8. The invention is further directed to the nucleic acid molecule in the form of an expression vehicle, as well as prokaryotic and eukaryotic hosts transformed with the nucleic acid molecule.

Also included in the present invention is a process for preparing an RPTP protein or glycoprotein of this invention, or a functional derivative thereof, comprising:

(a) culturing a host capable of expressing the protein, glycoprotein or functioanl derivative under culturing conditions;

(b) expressing the protein, glycprotein or functional derivative; and (c) recovering the protein, glycoprotein or functional derivative from the culture.

The invention is directed to an antibody, polyclonal, monoclonal, or chimeric, specific for the RPTPα protein or glycoprotein.

The invention is also directed to a method for detecting the presence of nucleic acid encoding a normal or mutant RPTP in a subject comprising:

(a) contacting a cell or an extract thereof from the subject with an oligonucleotide probe encoding at least a portion of the normal or mutant RPTP under hybridizing conditions; and (b) measuring the hybridization of the probe to the nucleic acid of the cell, thereby detecting the presence of the nucleic acid.

The DNA can be selectively amplified, using the polymerase chain reaction, prior to assay.

The invention is further directed to a method for detecting the presence, or measuring the quantity of an RPTP in cell or in a subject comprising:

(a) contacting said cell or an extract thereof with an antibody specific for an epitope of the RPTP; and (b) detecting the binding of the antibody to the cell or extract thereof, or measuring the quantity of antibody bound, thereby detecting the presence or measuring the quantity of the RPTP.

The present invention is also directed to methods for identifying and isolating a compound capable of binding to an RPTP from a chemical or biological preparation comprising:

(a) attaching the RPTP or the ligand-binding portion thereof to a solid phase matrix;

(b) contacting the chemical or biological preparation with the solid phase matrix allowing the compound to bind, and washing away any unbound material;

(c) detecting the presence of the compound bound to the solid phase; and, for purposes of isolation, (d) eluting the bound compound, thereby isolating the compound.

Finally, the invention includes a method for identifying a compound capable of stimulating or inhibiting the enzymatic activity of a RPTP, comprising:

(a) contacting the compound with the RPTP in pure form, in a membrane preparation, or in a whole live or fixed cell;

(b) incubating the mixture in step (a) for a sufficient interval;

(c) measuring the enzymatic activity of the RPTP;

(d) comparing the enzymatic activity to that of the RPTP incubated without the compound, thereby determining whether the compound stimulates or inhibits the activity.

In all the above methods, the RPTP is preferably RPTPα, most preferably, human RPTPα.

4. DESCRIPTION OF THE FIGURES

Figure 1A:
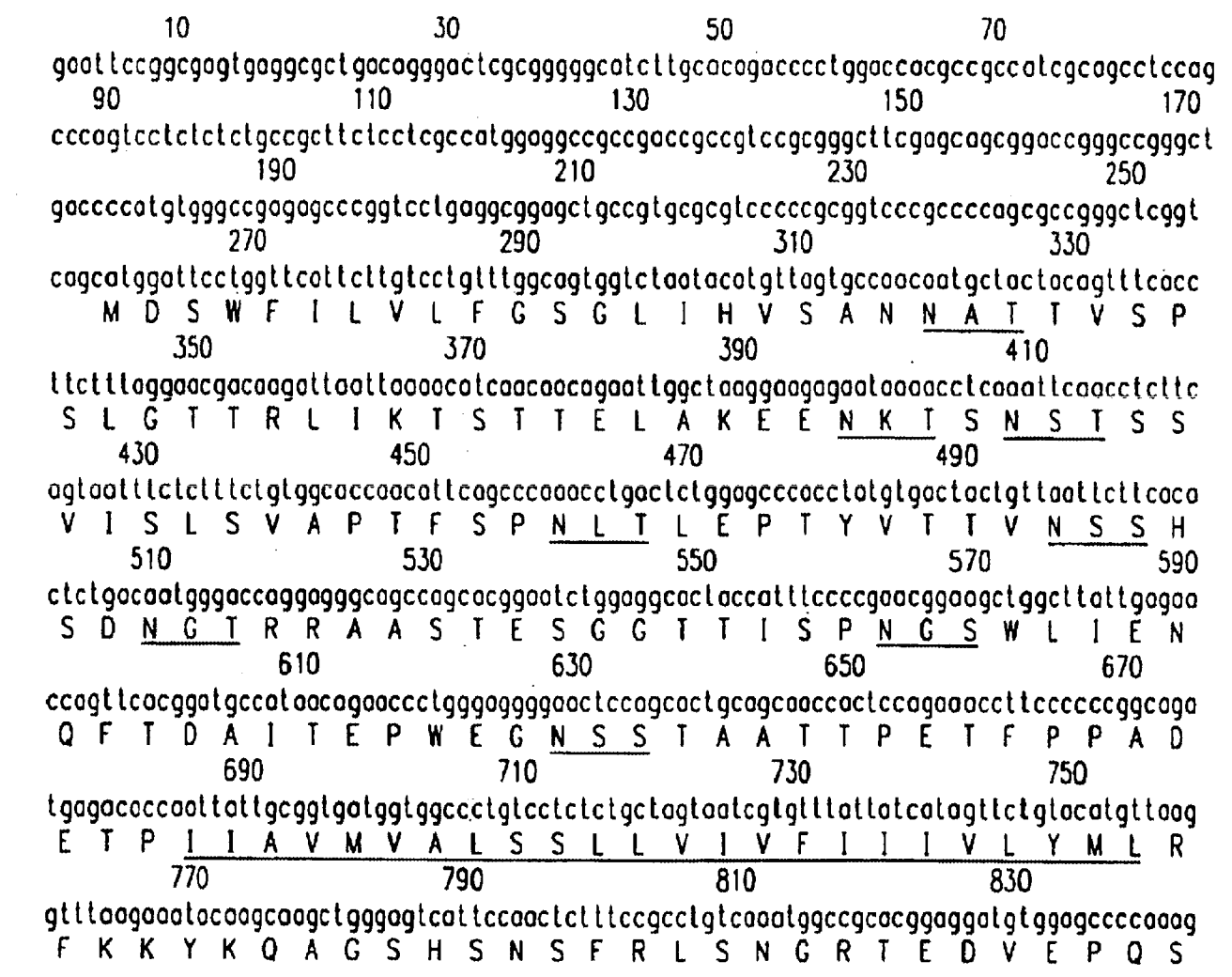

FIG. 1 shows the nucleotide sequence (SEQ ID NO:4) and predicted amino acid sequence (SEQ ID NO:3) of murine RPTPα. FIG. 1A (1A(1)–1A((3)) shows the sequence of the phage λ-109 cDNA insert (numbering refers to nucleotide positions) and predicted RPTPα protein sequence (using the standard one-letter amino acid code). The putative transmembrane domain (amino acids 143 to 166) is underlined as well as the potential N-linked glycosylation sites in the extracellular domain. The borders of homology between the tandemly repeated-PTPase domains (I and II) are indicated by square brackets. Cysteine (C) residues conserved in the catalytic domain of all known RPTPs are also underlined. FIG. 1B shows a schematic structure of a λ-109 cDNA clone containing the RPTPα coding sequence. RPTP domains I and II are indicated as black boxes, the transmembrane domain is shaded. The start of the N-terminally truncated PTP-ΔC protein (see FIG. 3, below) is indicated by an arrow (at amino acid 214). The positions of restriction sites used for generating nested deletions for sequencing are indicated. Abbreviations: TM, transmembrane domain; B, BamHI site; Bs, BstEII site; N, NcoI site; Nd, NdeI site; P, PstI site; R, EcoRI site; S: SacII site; St, StuI site.

FIG. 2 is a Northern blot showing expression of the murine RPTPα mRNA. 5 μg of Poly A+ RNA from mouse tissues and cell lines was fractionated on formaldehyde-containing agarose gels and subjected to Northern analysis using as a probe the entire RPTPα cDNA. The positions of the 28S and 18S ribosomal RNA are indicated. Lanes: 1, kidney; 2, lung; 3, heart; 4, stomach; 5, brain; 6, spleen; 7, liver; 8, NIH-3T3 fibroblast cell line (Honegger, A. M. et al. (1987) Cell 51, 199–209); 9, BAF prepro-B lymphoid cell line (Palacios, R. et al. (1985) Cell 41, 727–734).

Figure 3:
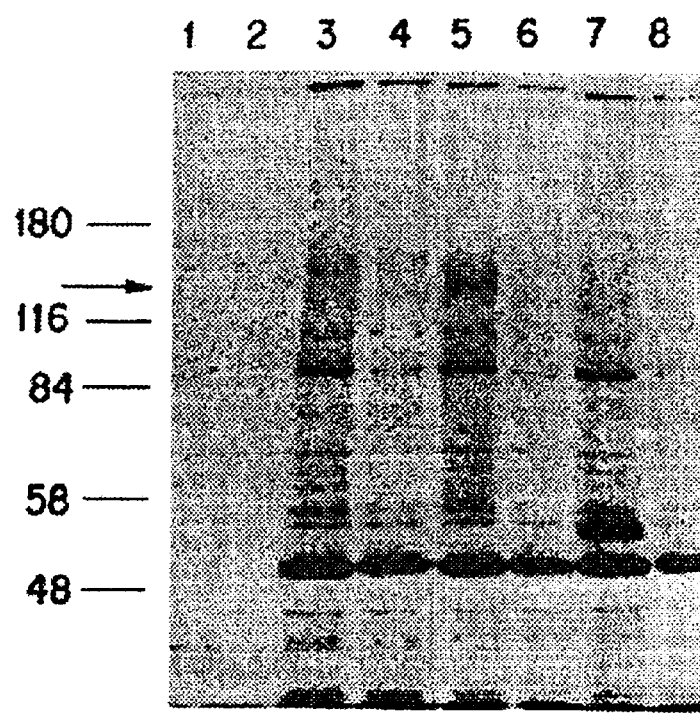

FIG. 3 is a gel pattern showing results of PAGE of immunoprecipitates of the murine RPTPα protein. COS cells were transiently transfected using the DEAE-dextran method with a negative control plasmid (expression vector pLSV without insert), with either pLSV-PTP-α (the same expression vector containing the RPTPα cDNA), or with the expression vector pLSVΔC, designed to express a truncated RPTPα protein (PTP-ΔC, amino-acids 214–794, from which the transmembrane and extracellular domains have been removed). After metabolic labelling with [$^{35}$S]-methionine, immunoprecipitation was performed using either pre-immune serum (lanes 1 and 2) or with an antiserum designated "2A" (lanes 3–8), raised against a synthetic peptide corresponding to the C-terminus of the RPTPα protein in the absence or presence of 100 μg of the immunizing peptide. Sizes of molecular weight markers are shown in kDa at the left margin. The arrow marks the position of the 130 kDa RPTPα protein (lane 5). Lane 1: pLSV, pre-immune serum; lane 2: pLSV-PTP-α, pre-immune serum; lane 3: pLSV, antiserum 2A; lane 4: pLSV, antiserum 2A in the presence of synthetic peptide; lane 5: pLSV-PTP-α, antiserum 2A; lane 6: pLSV-PTP-α, antiserum 2A in the presence of synthetic peptide; lane 7: pLSVΔC, antiserum 2A; lane 8: pLSVΔC, antiserum 2A in the presence of synthetic peptide.

FIG. 4 shows the structure of human RPTPα deduced from the sequence of cDNA clones. FIG. 4A is a composite restriction map [3615 base pairs (bp)] of overlapping clones 31-4 and 27-1, which together contain the entire coding region of human RPTPα. FIG. 4B shows the relative positions of clones 31-4 and 27-1. Both strands of each clone were sequenced in their entirety by using a series of oligonucleotide primers. The hatched region in clone 31-4 corresponds to the fragment used as probe for the Northern blot (see FIG. 6, below) as well as for the chromosome assignment. FIG. 4C shows the different domains of RPTPα. FIG. 4D provides a comparison of the amino acid sequences of human (line 1) [SEQ ID NO:1] and mouse (line 2) [SEQ ID NO:3] RPTPα. The single-letter amino acid code is used. Only the differences are shown. The dashed line indicates a stretch of amino acids not present in the mouse sequence. The coding portion of human RPTPα, and its position relative to clones 31-4 and 27-1 (FIG. 4B), is shown at the top. The following regions are designated in encircled Roman numerals: signal peptide (I), extracellular domain with potential N-glycosylation sites for the human protein underlined (II), transmembrane (III), juxtamembrane (IV), first phosphatase domain (V), interdomain (VI), second phosphatase domain (VII), C terminus (VIII).

FIG. 5 shows a comparison of the amino acid sequences of the first (FIG. 5A) and second (FIG. 5B) conserved phosphatase domains of human RPTPs LCA, α, β and γ. CON is the consensus sequence: a capital letter indicates complete agreement, while a small letter indicates agreement among two or three of the four sequences. A dash indicates lack of consensus.

Figure 6:
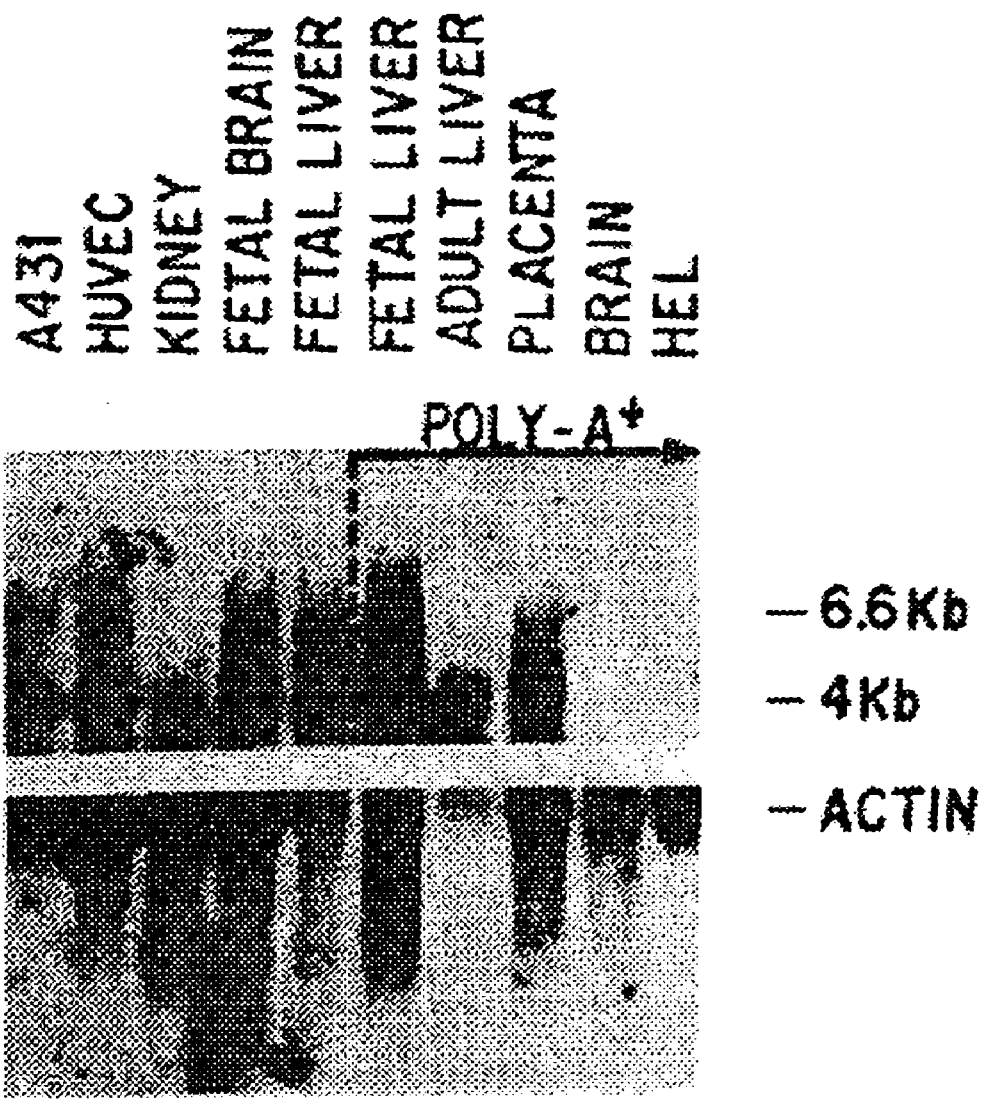

FIG. 6 shows a Northern blot pattern indicating relative expression of human RPTPα in various tissues and cell lines, as determined by hybridization with RPTPα probe (Upper) and β-actin probe (Lower). Total RNA (five left lanes) or poly (A)+ RNA (five right lanes) samples from the indicated human cell lines or tissues were analyzed. A431 is a human epidermoid carcinoma cell line; HEL is an erythroleukemia cell line; all other lanes represent flash-frozen tissues samples (HUVEC—human umbilical vein endothelial cells).

Figure 7:
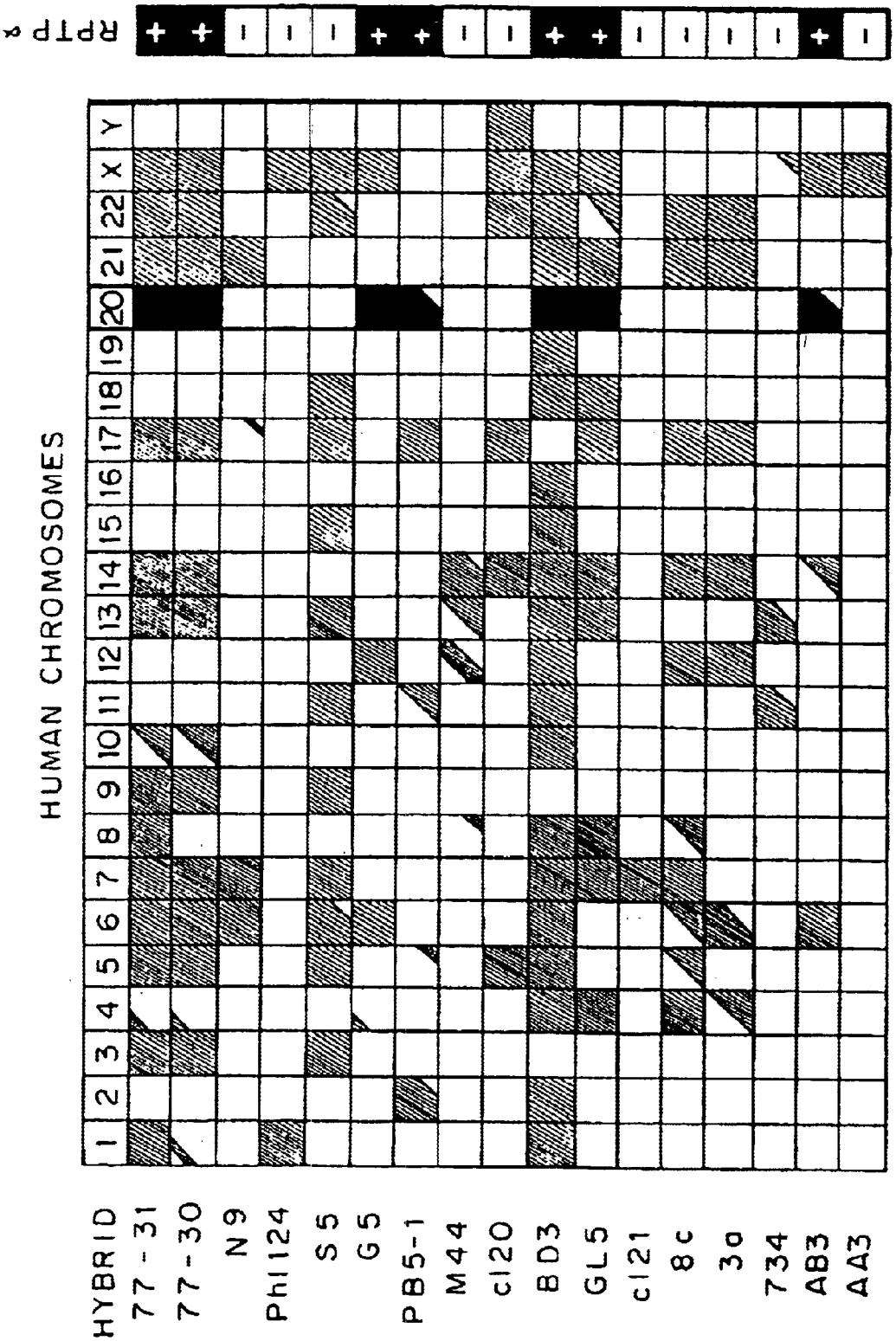

FIG. 7 is a matrix diagram which shows the chromosomal localization of human RPTPα based on analysis of a panel of 17 rodent-human somatic cell hybrids. A completely stippled box indicates that the hybrid contained the human chromosome indicated in the upper row; lower-right stippling indicates presence of the long arm of (or part of the long arm, indicated by a smaller fraction of stippling) of the chromosome; upper-left stippling indicates presence of the short arm (or partial short arm) of the chromosome; an open box indicates absence of the chromosome. The boxes in the column for chromosome 20 are blackened to highlight correlation of presence of this chromosome (or chromosome region) with the presence of the RPTPα gene. The pattern of retention of the human RPTPα sequences in the hybrids is shown at right (RPTPα): presence of the gene is indicated by a "+" in a black box; absence of the gene is indicated by a "−" in an open box.

FIG. 8 shows the complete nucleotide sequence (SEQ ID NO:2) and deduced amino acid sequence (SEQ ID NO:1) of human RPTPα.

5. DETAILED DESCRIPTION OF THE INVENTION

Through the use of recombinant DNA methods, the present inventors have identified novel mammalian receptor-type (transmembrane) protein tyrosine phosphatases (PTPase; EC 3.1.3.48). The murine RPTPα has 794 amino acids, whereas the human RPTPα has 802 amino acids. In view of its receptor-like structure, and the likelihood that it is part of a family, the inventors have termed this protein, RPTPα (receptor protein tyrosine phosphatase alpha). The family is designated herein as "RPTP."

RPTPα has an intracellular domain homologous to the catalytic domains of other tyrosine phosphatases. The inventors have further characterized the 142 amino acid extracellular domain (including signal peptide) as having a high serine and threonine content (32%) and 8 potential N-glycosylation sites. The inventors have produced cDNA clones coding for the novel protein, and expressed the protein from eukaryotic hosts. Northern analysis has been used to identify the natural expression of the protein in various cells and tissues. They have further produced a polyclonal antibody to the protein by immunization with a synthetic peptide of RPTPα, which identifies a 130 kDa protein in cells transfected with a cDNA clone encoding a portion of RPTPα.

Remarkably, in addition to being composed of intracellular domains having enzymatic activity, the receptor family to which RPTPs belong includes transmembrane proteins having and N-terminal extracellular domains; this is analogous to the tyrosine kinase enzyme family (Tonks, N. K. et al. (1988) *Biochemistry* 27, 8695–8701; Charbonneau, H. et al. (1988) *Proc. Natl. Acad. Sci. USA* 85, 7182–7186; Streuli, M. et al., (1988) *J. Exp. Med.* 168, 1523–2530; Streuli, M. et al., (1989) *Proc. Natl. Acad. Sci. USA* 86, 8698–8702). The present inventors have therefore concluded that ligands in the extracellular environment can control the activity of this membrane-associated subclass of PTPases.

RPTPα and the other RPTPs of the present invention are useful in methods for screening drugs and other agents which are capable of activating or inhibiting the RPTP activity, and thereby affecting major pathways of cellular metabolism. By attaching an intact RPTP, or the ligand-binding portion thereof, to a solid phase matrix, an affinity probe is created which can be used to screen biological products or chemical agents for their capacity to interact with the receptor on the basis of their binding activity. Bound material can then be eluted from the affinity probe in purified form.

Methods for coupling proteins and peptides to the solid phase, the solid phase substances useful in these methods, and means for elution, are well known to those of skill in the art.

The RPTP protein or derivatives thereof having enzymatic activity can be used for testing of compounds capable of enhancing or inhibiting the phosphatase activity. The ability of a compound under test to modify phosphatase activity can be tested in an in vitro system wherein the test compound is added to purified RPTP protein or enzymatically active derivatives thereof, and the affects on enzyme activity measured using standard enzymological procedures well known to those of skill in the art.

Alternatively, the action of a compound on RPTP activity can be measured in a whole cell preparation using live or fixed cells, or a membrane fraction derived from live or fixed cells. This method is useful for screening compounds acting via the extracellular receptor portion of the protein, as well as compounds acting directly on the enzymatic portion of the protein. A test compound is incubated with cells, or with a membrane preparation derived therefrom, which express high amounts of the RPTP of this invention, such as transfected COS or NIH-3T3 cells. The amount of cellular phosphotyrosine is then measured, using methods well-known in the art (Honegger, A. M. et al., *Cell* 51:199–209 (1987); Margolis, B. et al., *Cell* 57:1101–1107 (1989)). The results are compared to results obtained in the absence of the test compound, or in the absence or presence of a known activator of RPTP enzymatic activity. In such studies, the action of the test compound in the presence of an activator of tyrosine kinase can also be measured.

A compound which stimulates RPTP activity will result in a net decrease in the amount of phosphotyrosine, whereas a compound which inhibits RPTP activity will result in a net increase in the amount of phosphotyrosine.

In the case of growth factor receptors which are tyrosine kinases, such as the receptors for epidermal growth factor (EGF) and for platelet-derived growth factor (PDGP), tyrosine phosphorylation is linked to cell growth and to oncogenic transformation. Activation of a PTPase, leading to dephosphorylation, would serve as a counterregulatory mechanism to prevent or inhibit growth, and might serve as an endogenous regulatory mechanism against cancer. Thus, mutation or dysregulation of this receptor/enzyme system may promote susceptibility to cancer The insulin receptor is also a tyrosine kinase, and phosphorylation of tyrosine in cells bearing insulin receptors would be associated with normal physiological function. In contrast to the case of cell growth and cancer, activation of an RPTP would counteract insulin effects. Subnormal RPTP levels or enzymatic activity would act to remove a normal counterregulatory mechanisms. Perhaps more important, though, over-activity, or inappropriate activation, of a RPTP would be expected to inhibit or totally prevent the action of insulin on cells, leading to diabetes (of an insulin-resistant variety). Thus, susceptibility to diabetes may be associated with RPTP dysregulation.

Therefore, the methods of the present invention for identifying normal or mutant RPTP genes, or for measuring the amount or activity of RPTP associated with a cell or tissue, can serve as methods for identifying susceptibility to cancer, diabetes, or other diseases associated with alterations in cellular phosphotyrosine metabolism.

The present invention provides methods for evaluating the presence and the level of normal or mutant RPTP in a subject. Absence, or more typically, low expression of the RPTP, or presence of a mutant RPTP, in an individual may serve as an important predictor of susceptibility to oncogenic transformation and the development of cancer. Alternatively, over-expression of RPTP, possibly due to a mutant receptor/enzyme system insensitive to negative regulation, or due to overabundance of a stimulatory ligand in the body, may serve as an important predictor of susceptibility to diabetes.

Oligonucleotide probes encoding various portions of the RPTP (see below) are used to test cells from a subject for the presence DNA or RNA sequences encoding the RPTP. A preferred probe would be one directed to the nucleic acid sequence encoding at least 4 amino acid residues, and preferably at least 5 amino acid residues, of the RPTPα or other RPTP protein of the present invention. Qualitative or quantitative assays can be performed using such probes. For example, Northern analysis (see Examples III and VI, below) is used to measure expression of an RPTP mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al. *Molecular Cloning: A Laboratory Manual*, Second Edition, Cold Spring Harbor Press, Cold Spring Harbor, N.Y. (1989), which references are herein incorporated by reference).

Recently, an in vitro, enzymatic method has been described which is capable of increasing the concentration of such desired nucleic acid molecules. This method has been referred to as the "polymerase chain reaction or "PCR" (Mullis, K. et al., *Cold Spring Harbor Symp. Quant. Biol.* 51:263–273 (1986); Erlich, H. et al., EP 50,424; EP 84,796, EP 258,017, EP 237,362; Mullis, K., EP 201,184; Mullis, K. et al., U.S. Pat. No. 4,683,202; Erlich, H., U.S. Pat. No. 4,582,788; and Saiki, R. et al., U.S. Pat. No. 4,683,194).

The polymerase chain reaction provides a method for selectively increasing the concentration of a particular nucleic acid sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate groups of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR method are selected such that they contain sequences identical to, or complementary to, sequences which flank the particular nucleic acid sequence whose amplification is desired.

More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature any double-stranded molecules which may be present. The "first" and "second" probes are then added to the sample at a concentration which greatly exceeds that of the desired nucleic acid molecule. When the sample is incubated under conditions conducive to hybridization and.polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second" probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Meth. Enzymol.* 155:335–350 (1987)).

In one embodiment, the invention is directed to a naturally occurring mammalian RPTPα. In another embodiment, the invention is directed to a recombinant mammalian RPTPα. The preferred RPTPs of the present invention are of human origin. The invention provides the naturally occurring molecule substantially free of other proteins with which it is natively associated. "Substantially free of other proteins or glycoproteins" indicates that the protein has been purified away from at least 90 per cent (on a weight basis), and from even at least 99 per cent if desired, of other proteins and glycoproteins with which it is natively associated, and is therefore substantially free of them. That can be achieved by subjecting the cells, tissue or fluids containing the RPTP to standard protein purification techniques such as immunoadsorbent columns bearing monoclonal antibodies reactive against the protein. Other forms of affinity purification can utilize solid-phase substrates which can bind the PTPase domain, or a ligand that will bind to the receptor domain. Alternatively, the purification can be achieved by a combination of standard methods, such as ammonium sulfate precipitation, molecular sieve chromatography, and ion exchange chromatography.

It will be understood that the mammalian RPTP of the present invention can be biochemically purified from a variety of cell or tissue sources. For preparation of naturally occurring RPTP, tissues such as mammalian placenta or brain, especially of human origin, are preferred.

Alternatively, because the gene for the RPTP can be isolated or synthesized, the polypeptide can be synthesized substantially free of other proteins or glycoproteins of mammalian origin in a prokaryotic organism or in a non-mammalian eukaryotic organism, if desired. As intended by the present invention, a recombinant RPTPα molecule produced in mammalian cells, such as transfected COS, NIH-3T3, or CHO cells, for example, is either a naturally occurring protein sequence or a functional derivative thereof. Where a naturally occurring protein or glycoprotein is produced by recombinant means, it is provided substantially free of the other proteins and glycoproteins with which it is natively associated.

Alternatively, methods are well known for the synthesis of polypeptides of desired sequence on solid phase supports and their subsequent separation from the support.

In a further embodiment, the invention provides "functional derivatives" of the RPTP. By "functional derivative" is meant a "fragment," "variant," "analog," or "chemical derivative" of the RPTP, which terms are defined below. A functional derivative retains at least a portion of the function of the RPTP, such as binding to a specific antibody, phosphatase enzymatic activity or binding of the extracellular domain to a ligand, which permits its utility in accordance with the present invention.

A "fragment" of the RPTP refers to any subset of the molecule, that is, a shorter peptide.

A "variant" of the RPTP refers to a molecule substantially similar to either the entire peptide or a fragment thereof. Variant peptides may be conveniently prepared by direct chemical synthesis of the variant peptide, using methods well-known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

An "analog" of the RPTP refers to a non-natural molecule substantially similar to either the entire molecule or a fragment thereof.

A "chemical derivative" of the RPTP contains additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or to other macromolecular carriers. Commonly used cross-linking agents include, e.g., 1,1-bis(diazoacetyl)-2- phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidyl-propionate), and bifunctional maleimides such as bis-N-maleimido-1,8-octane. Derivatizing agents such as methyl-3-[(p-azidophenyl) dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691, 016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W.H. Freeman & Co., San Francisco, pp. 79–86 (1983)), acetylation of the N-terminal amine, and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980)

This invention is also directed to an antibody specific for an epitope of RPTP, preferably, of RPTPα, most preferably of human RPTPα, and the use of such antibody to detect the presence of, or measure the quantity or concentration of, the RPTP in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, GILD and any subclass thereof. The hybridoma producing the mAbs of this invention may be cultivated in vitro or in vivo. Production of high titers of mAbs in vivo production makes this the presently preferred method of production. Briefly, cells from the individual hybridomas are injected intraperitoneally into pristane-primed BALB/c mice to produce ascites fluid containing high concentrations of the desired mAbs. MAbs of isotype IgM or IgG may be purified from such ascites fluids, or from culture supernatants, using column chromatography methods well known to those of skill in the art.

Chimeric antibodies are molecules different portions of which are derived from different animal species, such as those having variable region derived from a murine mAb and a human immunoglobulin constant region. Chimeric antibodies and methods for their production are known in the art (Cabilly et al, *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 86/01533 (published Mar. 13, 1986); Kudo et al., European Patent Application 184187 (published Jun. 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the RPTP of the present invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a RPTP epitope.

The anti-Id mAbs thus have their own idiotypic epitopes, or "idiotopes" structurally similar to the epitope being evaluated, such as RPTPα.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of RPTP according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively or qualitatively detect the presence of cells which express the RPTP protein. This can be accomplished by immunofluorescence techniques employing a fluorescently labeled antibody (see below) coupled with light microscopic, flow cytometric, or fluorimetric detection.

The antibodies (of fragments thereof) useful in the present invention may be employed histologically, as in immunofluorescence or immunoelectron microscopy, for in situ detection of RPTP. In situ detection may be accomplished by removing a histological specimen from a patient, and providing.the a labeled antibody of the present invention to such a specimen. The antibody (or fragment) is preferably provided by applying or by overlaying the labeled antibody (or fragment) to a biological sample. Through the use of such a procedure, it is possible to determine not only the presence of the RPTP but also its distribution on the examined tissue. Using the present invention, those of ordinary skill will readily perceive that any of a wide variety of histological methods (such as staining procedures) can be modified in order to achieve such in situ detection. Such assays for RPTP typically comprises incubating a biological sample, such as a biological fluid, a tissue extract, freshly harvested cells such as lymphocytes or leucocytes, or cells which have been incubated in tissue culture, in the presence of a detectably labeled antibody capable of identifying RPTP, and detecting the antibody by any of a number of techniques well-known in the art.

The biological sample may be treated with a solid phase support such as nitrocellulose, or other solid support which is capable of immobilizing cells, cell particles or soluble proteins. The support may then be washed with suitable buffers followed by treatment with the detectably labeled RPTP-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-RPTP antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the RPTP-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect an RPTP through the use of a radioimmunoassay (RIA) (see, for example, Work, T. S. et al., *Laboratory Techniques and Biochemistry in Molecular Biology*, North Holland Publishing Company, New York, 1978, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncompleted labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning RPTP in a subject can also be tested using direct enzymatic assays, for the tyrosine phosphatase activity. Such biochemical measurements can be performed in vitro, using purified enzymes, allowing precise measurements of enzyme activity, or with membrane preparations, or whole cells, where the net phosphotyrosine level is determined.

In additional embodiments of the present invention, a DNA sequence encoding a RPTP molecule and methods for expressing the DNA sequence are provided. One of ordinary skill in the art will know how to identify and clone additional RPTP molecules, of human or other mammalian species, which have sequence homology to the RPTP molecules described herein, using the genetic sequences and oligonucleotides of the present invention without undue experimentation. Furthermore, manipulation of the genetic constructs of the present invention allow the grafting of a particular ligand-binding receptor domain onto the transmembrane and catalytic portions of the RPTP resulting in chimeric molecules. Non-limiting examples of such chimeric molecules include the RPTP wherein the receptor is an epidermal growth factor receptor, a fibroblast growth factor receptor, and the like. Genetically engineered chimeric receptors are known in the art (see, for example, Riedel, H. et al., Nature 324:628–670 (1986)).

Genetic constructs encoding RPTPα, functional derivative thereof, and chimeric molecules such as those described above, can be used in gene therapy. An abnormal or dysfunctional RPTP, which results in disease, may be replaced by infusion of cells of the desired lineage (such as hemopoietic cells, for example) transfected with a normal RPTP. Alternatively, or additionally, cells carrying a chimeric RPTP having a receptor to a ligand of choice (e.g. EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed by Sambrook et al. (supra).

The 3' terminus of the recombinant molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form (i.e. a sheet, rod, sphere, ovoid, etc. Procedures for such immobilization are well known to those of ordinary skill. In the most preferred embodiment, the 3' end of the recombinant molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of such recombinant molecule to the support.

Oligonucleotides representing a portion of an RPTP are useful for screening for the presence of genes encoding such proteins and for the cloning of RPTP genes. Techniques for synthesizing such oligonucleotides are disclosed by, for example, Wu, R., et al., *Prog. Nucl. Acid. Res. Molec. Biol.* 21:101–141 (1978)).

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene*, 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lathe, R., et al., *J. Molec. Biol.*

183:1–12 (1985). Using the "codon usage rules" of Lathe, a single oligonucleotide, or a set of oligonucleotides, that contains a theoretical "most probable" nucleotide sequence capable of encoding the RPTP sequences is identified.

Although occasionally an amino acid sequences may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding the RPTP fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the RPTP gene (Sambrook et al., supra).

A suitable oligonucleotide, or set of oligonucleotides, which is capable of encoding a fragment of the RPTP gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the RPTP gene. Single stranded oligonucleotide molecules complementary to the "most probable" RPTP peptide encoding sequences can be synthesized using procedures which are well known to those of ordinary skill in the art (Belagaje, R., et al., *J. Biol. Chem.* 254:5765–5780 (1979); Maniatis, T., et al., In: *Molecular Mechanisms in the Control of Gene Expression*, Nierlich, D. P., et al., Eds., Acad. Press, NY (1976); Wu, R., et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Haymes, B. D., et al. (In: *Nucleic Acid Hybridization, A Practical Approach*, IRL Press, Washington, D.C. (1985)), which references are herein incorporated by reference. Techniques such as, or similar to, those described above have successfully enabled the cloning of genes for human aldehyde dehydrogenases (Hsu, L. C., et al., *Proc. Natl. Acad. Sci. USA* 82:3771–3775 (1985)), fibronectin (Suzuki, S., et al., *EMBO J.* 4:2519–2524 (1985)), the human estrogen receptor gene (Walter, P., et al., *Proc. Natl. Acad. Sci. USA* 82:7889–7893 (1985)), tissue-type plasminogen activator (Pennica, D., et al., *Nature* 301:214–221 (1983)) and human term placental alkaline phosphatase complementary DNA (Kam, W., et al., *Proc. Natl. Acad. Sci. USA* 82:(715–8719 (1985)).

In a alternative way of cloning the RPTP gene, a library of expression vectors is prepared by cloning DNA or, more preferably, cDNA (from a cell capable of expressing RPTP) into an expression vector. The library is then screened for members capable of expressing a protein which binds to anti-RPTP antibody, and which has a nucleotide sequence that is capable of encoding polypeptides that have the same amino acid sequence as RPTP, or fragments thereof. In this embodiment, DNA, or more preferably cDNA, is extracted and purified from a cell which is capable of expressing RPTP protein. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translational control sequences) is capable of expressing a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing RPTP in order to produce a prokaryotic genomic expression vector library. Procedures for preparing cDNA and for producing a genomic library are disclosed by Sambrook et al. (supra).

A DNA sequence encoding the RPTP of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a RPTP-encoding sequence) are said to be operably linked if the nature of the linkage between the two DNA sequences does not (1) result in the introduction of a frame-shift mutation, (2) interfere with the ability of the promoter region sequence to direct the transcription of the RPTP gene sequence, or (3) interfere with the ability of the RPTP gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA molecule which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or, of a "promoter sequence," a double-stranded molecule is created which will contain a functional promoter, if that extension proceeds towards the "promoter sequence" or the "promoter sequence complement." This functional promoter will direct the transcription of a nucleic acid molecule which is operably linked to that strand of the double-stranded molecule which contains the "promoter sequence" (and not that strand of the molecule which contains the "promoter sequence complement" ).

Certain RNA polymerases exhibit a high specificity for such promoters. The RNA polymerases of the bacteriophages T7, T3, and SP-6 are especially well characterized, and exhibit high promoter specificity. The promoter sequences which are specific for each of these RNA polymerases also direct the polymerase to utilize (i.e. transcribe) only one strand of the two strands of a duplex DNA template. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

Thus, as indicated above, in order to function as a promoter, a promoter sequence must be present as a double-stranded molecule. For the purposes of the present invention, the two strands of a functional promoter sequence are referred to as a "transcript" strand and a "complementary" strand. The "transcript" strand is that strand of the duplex which will be transcribed by the RNA polymerase (i.e. which serves as the template for transcription). The "complementary" strand is the strand which has a sequence complementary to the "transcript" strand, and which must be present, and hybridized to the "transcript" strand, in order for transcription to occur. Thus, when the "transcript" strand of a promoter sequence is operably linked to a second sequence, hybridization of the "transcript" strand with the "complement" strand, will, in the presence of a polymerase, result in the transcription of the "transcript" strand, and will produce an RNA transcript using the sequence of the "transcript" strand as a template.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81:2035–2039 (1984)) polymerases; the $P_R$ and $P_L$ promoters of bacteriophage λ (*The Bacteriophage Lambda*, Hershey, A. D., Ed., Cold Spring Harbor Press, Cold Spring Harbor, N.Y. (1973); *Lambda II*, Hendrix, R. W., Ed., Cold Spring Harbor Press, Cold Spring Harbor, N.Y. (1980)); the trp , recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of Bacillus (Gryczan, T. J., In: *The Molecular Biology of the Bacilli*, Academic Press, Inc., NY (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); and the yeast gal4 gene promoter (Johnston, S. A., et al., *Proc. Natl. Acad. Sci. (USA)* 79:6971–6975 (1982); Silver, P. A., et al., *Proc. Natl. Acad. Sci. (USA)* 81:5951–5955 (1984)). All of the above listed references are incorporated by reference herein.

Strong promoters are preferred. Examples of such preferred promoters are those which recognize the T3, SP6 and T7 polymerases, the $P_L$ promoter of bacteriophage λ, the recA promoter and the promoter of the mouse metallothionein I gene. A most preferred promoter for eukaryotic expression of RPTP is an SV40 promoter such as that driving transcription in the pLSV vector (Livneh, E., et al., (1986) *J. Biol. Chem.* 261, 12490–12497). The sequences of such polymerase recognition sites are disclosed by Watson, J. D. et al. (In: *Molecular Biology of the Gene*, Fourth Edition, Benjamin/Cummings Publishing Co., Inc., Menlo Park, Calif., (1987)).

Having now generally described the invention, the same will be more readily understood through reference to the following example which is provided by way of illustration, and is not intended to be limiting of the present invention, unless specified.

6. EXAMPLE: ISOLATION AND ANALYSIS OF MURINE RPTPα cDNA CLONES

6.1. Library Screening

A mouse BALB/C brain cDNA library in λgt11 (obtained from Dr. Y. Citri) was screened at relaxed stringency (6×SSC, 5×Denhardts, 0.1% SDS, 50 mM Tris pH 7.5, 1 mM EDTA, 0.1 mg/ml salmon sperm DNA, hybridization temperature 50° C.) using as a probe a 2400 bp BglII-AccI fragment representing the intracellular and trans-membrane domains of the human T200 glycoprotein (Ralph, S. J. et al., (1987) *EMBO J.* 6, 1251–1257), which had been $^{32}$P-labeled using the random-priming method. Washing was performed at 50° C. in 6×SSC, 0.1% SDS. Out of $10^6$ clones, 51 positives were picked, selected and characterized by restriction enzyme mapping. EcoRI fragments of 0.95, 1.6 and 0.3 Kb isolated from the phage clone containing the longest insert (λ-109) were subcloned into the Bluescript KS plus and minus vectors. A series of nested deletions were generated by taking use of restriction sites common to the cloned cDNA fragments and the polylinker region of the plasmid vector. The individual restriction sites used are indicated in FIG. 1*b*. Single stranded DNA was prepared from these constructs, and used as a template for sequence analysis using the dideoxynucleotide chain termination method (Sequenase, United States Biochemical). All regions were sequenced on both strands. The relative order and orientation of the EcoRI fragments in the recombinant phage was determined by restriction mapping. To ascertain that the different EcoRI fragments did not correspond to unrelated cDNA fragments ligated together during the process of library construction, restriction mapping was also performed on a different and independent isolate, λ-113.

6.2. Results

Brain tissue already has proven to be a rich source of many types of tyrosine kinases, and recent biochemical evidence has also indicated the existence of multiple forms of PTPase activity (Jones, S. W. et al., (1989) *J. Biol. Chem.* 264, 7747–7753). In order to search for new receptor-type PTPase, the present inventors screened at low stringency a mouse brain cDNA library, using as a hybridization probe the intracellular domain of human CD45 containing two tandem PTPase domains (Tonks, N. K. et al., supra; Charbonneau, H. et al., supra; Ralph, S. J. et al., supra). Positive clones were classified by cross-hybridization and restriction mapping into several categories, and the longest phage insert (λ-109) corresponding to the most abundantly represented class was chosen for subcloning and further analysis.

The result of the nucleotide sequence analysis is shown in FIG. 1, which presents the nucleotide sequence (SEQ ID NO:4) and the amino acid sequence (SEQ ID NO:3) of murine RPTPα. Conceptual translation of the cDNA sequence reveals the existence of a major open reading frame of 794 amino acids, assuming that translation icnitiates at nucleotide 259 (an in-frame stop codon is present 60 nucleotides upstream). The putative initiation methionine codon is embedded in a relatively standard environment for initiation of translation (Kozak, M., (1987) *Nucl. Ac. Res.* 15, 8125–8148), and is followed by a characteristic hydrophobic stretch of amino acids which probably function as a signal peptide. According to the "−3,−1" rule (von Heijne, G. (1986) *Nucl. Ac. Res.* 14, 4683–4690), residues 20 and 25 are both likely candidates to constitute the N-terminus of the mature protein. A second hydrophobic stretch is found between amino acids 143 and 166, and is followed by a series of highly charged residues, consistent with the stop-transfer signals found to be associated with many membrane-spanning domains. The predicted intracellular domain of the protein consists of two tandem repeats having 44% sequence identity between each other (residues 259–486 and 552–776). Each of these repeats display significant sequence identity with the intracellular catalytic domains of the previously described transmembrane PTPase CD45 (Ralph, S. J. et al., supra) and LAR (Streuli, M. et al., (1988), supra) (45% and 53% amino acid sequence identity, respectively).

In contrast, the EMBL and GENBANK databases contain no significant homology to known sequences of the putative extracellular domain of the encoded protein. Features of the extracellular domain include a uniquely high content of serine and threonine residues (>32%), the absence of cysteine residues, and the presence of 8 potential N-linked glycosylation sites.

It was concluded that the isolated cDNA encoded a new member of the transmembrane PTPase family having a novel type of extracellular domain. In view of its receptor-like structure and the likelihood that additional members of this family can be found based on the present experimental evidence, the name muRPTPα (murine receptor protein tyrosine phosphatase-α) was chosen to designate this protein.

7. EXAMPLE: CHROMOSOMAL LOCALIZATION OF THE MOUSE RPTPα GENE

STS/A, 020/A, CXS and OXA recombinant inbred (RI) mice, and CXB RI strains N, O, P, Q, and R were a gift from Dr. Jo Hilgers (The Netherlands Cancer Institute). All other inbred mice were purchased from the Jackson Laboratory (Bar Harbor, Me.). Backcross (BC) animals were bred at New York University with inbred progenitors obtained from the Jackson Laboratory. The female parent is named first in all crosses and F1 designations.

Spleen genomic DNA from the AKXD, AKXL, BXD, BXH and G, H, I SWXL RI strains, and from CXB, RI strains D, E, G, H, I, J, and K was purchased from the DNA Resource at the Jackson Laboratory. For all other mice, genomic DNA was prepared from crude liver nuclei by a standard sequence of protease digestion, phenol and chloroform extraction, and ethanol precipitation. Mouse genomic DNAs were subjected to Southern blotting analysis by slight modifications of standard procedures, exactly as described previously (Silver, J. (1985) *J. Hered.* 76, 436–440). A 1.8 kb EcoRI fragment corresponding to the intracellular phosphatase domains of RPTPα, and a 0.7 kb SacII-EcoRI fragment corresponding to its extracellular and transmembrane domains, were cloned into the Bluescript KS vector, yielding plasmids p109 and p923, respectively.

DNA restriction fragment length variants associated with the Il-1a locus (interleukin-1 alpha) were detected by Southern blotting as described previously (D'Eustachio, P. et al., (1987) *Immunogenetics* 26, 339–343). The significance of deviations from 1:1 segregation for pairs of markers was calculated by the Bayesian method of Silver and Buckler (Silver, J. et al., (1986) *Proc. Natl. Acad. Sci. USA* 83, 1423–1427); Blank, R. D. et al., (1988) *Genetics* 120, 1073–1083). Map distances were estimated from recombination fractions measure in RI strain sets according to B. A. Taylor (in: Morse, H. C. III, ed., *Origins of Inbred Mice*, Academic Press, New York, 1978, pp. 423–438), and their associated 95% binomial confidence limits were calculated according to Silver (1985, supra). Probabilities of alternative orders of trios of markers were calculated according to D. Bishop ((1985) *Genet. Epidemiol.* 2, 349–361, equation 1). Computations were carried out on a VAX6000-410 computer.

Southern blotting analyses of genomic DNA from inbred strains of mice revealed two useful restriction length variants, one visualized with a probe corresponding to the intracellular domain of murine RPTPα (p109) and one visualized with an extracellular and transmembrane domains probe (p923). Together, these variants allowed definition of three allelic forms of muRPTPα among the 10 inbred strains of mice surveyed (Table I).

TABLE I

Restriction Fragment Length Variants Detected by muRPTPα Probes

| Allele | p109 | p923 | Mouse Strains |
|---|---|---|---|
| a | 9.4 | 5.9 + 4.2 | BALB/cJ |
| b | 6.5 | 4.2 + 1.8 | C57BL/6J, C57L/J, DBA/2J |
| c | 6.5 | 5.9 + 4.2 | C3H/HeJ, 020/A, AKR/J, SWR/J, SJL/J, STS/A |

Liver genomic DNA digested with TaqI restriction endonuclease was analyzed by Southern blotting. Fragment sizes in kilobases are shown.

Inheritance of these alleles in RI mice was scored. Comparison of the strain distribution patterns observed for murine RPTPα (Table II) with those previously observed for other markers of known chromosomal location in these mice indicated close linkage between the muRPTPα and Il-1a (Interleukin-1) loci on chromosome 2 (3 RI strains among 89 examined). This degree of concordance has a probability of less than 0.00001 of occurring as a chance event were the loci unlinked. The observed fraction of recombinant strains indicates a map distance of 0.9 cM between the loci (95% confidence limits 0.2–0.6 cM).

TABLE II

Inheritance of muRPTPα and Il-1a DNA sequence variants in RI strains of mice

AKXD strain:

| | 1 | 2 | 3 | 6 | 7 | 8 | 9 | 10 | 11 | 12 | 13 | 14 | 15 | 16 | 18 | 20 | 21 | 22 | 23 | 24 | 25 | 26 | 27 | 28 |
|---|---|---|---|---|---|---|---|---|---|---|---|---|---|---|---|---|---|---|---|---|---|---|---|---|
| Il-1a | D | D | D | A | D | A | A | D | D | A | D | A | D | A | D | A | D | A | D | A | D | A | A | A |
| R-PTP-α | D | D | D | A | D | A | A | D | A | A | D | A | D | A | D | A | D | A | D | A | D | A | A | A |

AKXL strain:

| | 5 | 6 | 7 | 8 | 9 | 12 | 13 | 14 | 16 | 17 | 19 | 21 | 24 | 25 | 28 | 29 | 37 | 38 |
|---|---|---|---|---|---|---|---|---|---|---|---|---|---|---|---|---|---|---|
| Il-1a | L | L | L | A | L | A | L | L | L | A | A | L | A | L | A | L | A | L |
| R-PTP-α | L | L | L | A | L | A | L | L | L | A | A | L | A | L | A | L | A | L |

SWXL strain:

| | 4 | 7 | 12 | 14 | 15 | 16 | 17 |
|---|---|---|---|---|---|---|---|
| Il-1a | S | L | S | L | L | S | L |
| R-PTP-α | S | L | S | L | L | S | L |

CXB strain:

| | D | E | G | H | I | J | K | N | O | P | Q | R |
|---|---|---|---|---|---|---|---|---|---|---|---|---|
| Il-1a | C | B | B | C | B | B | B | C | C | C | C | B |
| R-PTP-α | C | B | B | C | B | B | B | C | B | C | C | B |

CXS strain:

| | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Il-1a | T | T | T | C | C | T | T | T | C | T | C | C | T | C |
| R-PTP-α | T | T | T | C | C | T | C | T | C | T | C | C | T | C |

BXH STRAIN:

| | 2 | 3 | 4 | 6 | 7 | 8 | 9 | 10 | 11 | 12 | 14 | 19 |
|---|---|---|---|---|---|---|---|---|---|---|---|---|
| Il-1a | B | B | H | H | B | H | B | H | B | H | H | B |
| R-PTP-α | B | B | H | H | B | H | B | H | B | H | H | B |

BXJ strain:

| | 1 | 2 |
|---|---|---|
| Il-1a | B | B |
| R-PTP-α | B | B |

RI strains were typed for alleles of muRPTPα and Il-1a by Southern blotting of TaqI-digested DNA (see Table I and D'Eustachio, P. et al., Immunogenetics 26, 339–343 (1987)). Il-1a alleles for AKXD, CXB strains D–K, and BXH mice were disclosed in D'Eustachio et al., supra). All RI strains are homozygous for one of the progenitor strain alleles at each locus; the allele is indicated by an uppercase letter corresponding to the parent strain as follows: A, AKR/J; B, C57BL/6J; C, BALB/c; D, DBA/2J; H, C3H/HeJ; J, SJL/J; L, C57L/J; S, SWR/J; T, STS/A.

Following the inheritance of muRPTPα, Il-1a and a (nonagouti) among progeny of reciprocal backcross between the C57BL/6J and SWR/J strains confirmed the linkage of muRPTPα and Il-1a, and suggested an order for the two genes (Table III). Of 150 progeny, 14 were recombinant between muRPTPα and a, and one was recombinant between muRPTPα and Il-1a. If the locus order were: centromere—Il-1a—muRPTPα—a, these results would require the occurrence of no double crossovers; alternative orders require one or 14 such events, and, evaluated according to the method of Bishop (supra), are at least 9.5-fold less likely. The distance between Il-1a and muRPTPα, 0.6 cM (95% confidence limits: 0.1–2.4 cM), agrees within sampling fluctuation with the distance estimated from the RI strain data. Comparison of these results with results recently obtained for Bmp-2a (Bone morphogenic protein 2a, Dickinson, M. E. et al., (1990) *Genomics* 6, 505–520) suggests that the two genes may be closely linked, although there is no obvious structural homology between them.

TABLE III

Linkage Among Markers of Chromosome 2 in Backcross BC Progeny

A. ALLELE COMBINATIONS FROM $F_1$ PARENT AND THE ACTUAL NUMBERS OF C57BL/6J-DERIVED (b) AND SWR/J-DERIVED (s) ALLELES FOUND

| LOCUS | POSSIBLE ALLELE COMBINATION | | | | | | | | Σb | Σs |
|---|---|---|---|---|---|---|---|---|---|---|
| Il-1a | b | s | b | s | b | s | b | s | 76 | 74 |
| R-PTP-α | b | s | b | s | s | b | s | b | 77 | 73 |
| a | b | s | s | b | s | b | b | s | 69 | 81 |

B. NUMBERS OF PROGENY FROM EACH BACKCROSS THAT INHERITED EACH POSSIBLE ALLELE COMBINATION.

| BACKCROSS | NUMBER OF PROGENY | | | | | | | |
|---|---|---|---|---|---|---|---|---|
| $F_1 \times B$ | 44 | 43 | 9 | 1 | 0 | 1 | 0 | 0 |
| $B \times F_1$ | 21 | 27 | 2 | 2 | 0 | 0 | 0 | 0 |
| | | 135 | | 14 | | 1 | | 0 |

150 progeny from BC between (C57BL/6J × SWR/J)$F_1$ (F1) and C57BL/6J (B) mice were typed visually for inheritance of the nonagouti (a) marker and, by Southern blotting, for alleles of the muRPTPα and Il-1a loci.

8. EXAMPLE: EXPRESSION OF MURINE RPTPα RNA

8.1. Northern Analysis

Poly A$^+$ RNA was prepared from adult mouse tissues and cell lines by oligo(dT) selection as described (Vennström, B. et al., (1982) *Cell* 28, 135–143), fractionated (5 μg per lane) on a formaldehyde-containing gel and transferred to nitrocellulose (Hybond C, Amersham) using standard procedures. A $^{32}$P-labelled probe was prepared by primer extension on a single-stranded template consisting of the entire λ-109 cDNA cloned into the EcoRI site of the Bluescript vector in the antisense orientation, using the Klenow fragment of DNA polymerase for elongation from an annealed T7 primer, in the presence of $^{32}$P-dATP. Hybridization was performed at 42° C. in 50% formamide, 5×SSC, 25 mM KPO$_4$, 5×Denhardt's, 10 μg/ml salmon sperm DNA, and 10% sulfate. Washing was done at 48° C. in 0.1×SSC, 0.1% SDS. Higher stringency washes (58° C.) of the filter did not noticeably affect the hybridization pattern.

8.2. Expression of the Murine RPTPα Protein

The entire cDNA insert from phage λ-109 was released as one fragment from the phage using partial EcoRI digestion, and cloned into the Bluescript KS vector. A cDNA fragment lacking most of the untranslated leader sequence (starting from the Sac II site at position 226; see FIG. 1b) was subcloned into the SV40 promoter driven pLSV-vector (Livneh, E., et al., (1986) *J. Biol. Chem.* 261, 12490–12497), and the resulting plasmid DNA (pLSV-PTP-α) was transfected into COS cells using the DEAE-dextran method (Lopata, M. A. et al., (1984) *Nucl. Ac. Res.* 12, 5707–5717). The expression vector pLSVΔC encoding the N-terminally truncated muRPTPα protein was used as a control in the immunoprecipitation experiment.

8.3. Results

Poly A$^+$ RNA from various mouse tissues was prepared to study the expression of the muRPTPα gene. Northern analysis (FIG. 2) revealed a wide pattern of expression. A 3.0 kB mRNA was present in all tissues examined, except spleen, with brain and kidney showing the highest levels of expression. An mRNA of similar size could also be observed in the NIH-3T3 mouse fibroblast line, 2.2, and the prepro-B lymphoid cell line, BAF (FIG. 2). Shorter exposure of the Northern blot clearly showed that in addition a second mRNA species of very similar size (3.2 kb) is present in several tissues (e.g. brain) in lower amounts. The data also suggest that, although a poly A tail and a polyadenylation signal at the 3' end of the cDNA sequence were not observed, the isolated cDNA clone (2872 nucleotides) closely matches the full length of the mRNA.

9. EXAMPLE: TRANSIENT EXPRESSION OF THE MURINE RPTPα PROTEIN

9.1. Antibody Preparation and Immunoprecipitation

Rabbits were injected with a synthetic peptide corresponding to the predicted C-terminus of the muRPTPα protein (residues 777–794) coupled to BSA using EDCI (1-ethyl-3-(dimethylaminopropyl)carbodiimide) as a coupling reagent. Antigen was injected intradermally and subcutaneously in an emulsion of 1 mg peptide and complete Freund's adjuvant. Three booster injections were given at 2–3 week intervals with 0.5 mg peptide and incomplete adjuvant. An antiserum obtained using this method was designated "2A." Metabolic [$^{35}$S]-methionine labelling, cell extract preparation (60 hours after transfection) and indirect immunoprecipitation using protein-A-Sepharose were performed using standard procedures (Yarden, Y. et al., (1987) *EMBO J.* 6, 3341–3351).

9.2. Results

In order to determine the size of the mature protein, we cloned the muRPTPα cDNA with the exception of most of the untranslated leader into the pLSV vector (Livneh, E., et al., (1986) *J. Biol. Chem.* 261, 12490–12497) under the control of the SV40 promoter, yielding the expression vector pLSV-PTP-α. The vector was transfected into COS cells, and 60 hours later [$^{35}$S]-methionine labelled total cell extracts were prepared for immunoprecipitation, using antiserum 2A.

As seen in FIG. 3, the antiserum recognized several bands, one of which, a diffuse band of 130 kDa (arrow), was only present in immunoprecipitates from transfected cells (lane 5), but not from mock-transfected cells (lane 3) (transfected with pLSV without the muRPTPα cDNA). Precipitation could be competed out by the peptide used for immunization (lane 6).

The difference between the predicted (88 kDa) and observed (130 kDa) molecular weights for the muRPTPα protein is ascribed to its extensive glycosylation.

As an additional control for the specificity of the antiserum, we also transfected COS cells with a N-truncated version of the muRPTPα cDNA (starting at amino acid 214, and thus lacking the transmembrane and extracellular domains) in the same vector. A new and abundant protein with an apparent molecular weight of 55 kDa appeared in immunoprecipitates from cells transfected with this vector, which was again competed out by the antigenic peptide (lanes 7 and 8). The higher abundance of the truncated protein as compared to the mature muRPTPα protein was a consistent observation over several independent transfection experiments.

9.3. General Discussion for Sections 6–9

The Examples presented above describe the identification of a novel receptor-like PTPase, RPTPα, having a broad pattern of expression. RPTPs are therefore expected to have widespread functions beyond the regulation of lymphoid cell activity, as was previously thought based on study of CD45.

Studies using monoclonal antibodies directed against the extracellular domain of CD45 proteins showed that cross-linking of RPTPs can have profound effects on various cellular activities, although a direct effect on PTPase enzymatic activity remains to be shown. However, since ligand-induced receptor clustering is a central event in transmembrane signalling by receptor tyrosine kinases (Ullrich, A. et al., supra), it is proposed by the inventors that putative extracellular ligands for RPTPs have the capacity to regulate the activity of RPTPs in vivo.

In a manner analogous to that proposed for receptor tyrosine kinases (PTKs), RPTPs are proposed to have arisen through several gene fusion events between an ancestral PTPase domain, and domains capable of binding extracellular ligands (Ullrich, A. et al., Hanks, S. K. et al., supra).

The variety of extracellular domains potentially joined to PTPase domains to form receptor-like proteins are expected to reflect the range of possible ligands able to act by similar mechanisms. The availability of cloned RPTPs, such as those disclosed herein, will be valuable in determining their substrate specificity and in understanding their function and manipulating their activity.

RPTPs might have a broad specificity directed towards major tyrosine kinase substrates, with their different extracellular domains mainly allowing for different regulatory mechanisms responsive to different signals in the extracellular environment. Based on this view, they are expected to modulate the responsiveness of a cell to those polypeptide growth factors which act through receptor protein tyrosine kinases. As with PTK's, ligand binding would lead to an activation of enzymatic activity. Viewed in this light, RPTPα and molecules like it, would be negative growth regulators and can be considered potential recessive oncogenes.

For instance, deletion of portions of murine chromosome 2, to which RPTPα maps, appears to be an early event in the development of radiation-induced myeloid leukemia in SJL/J mice (Tracktenbrot, L. et al., (1988) *Leukemia* 2, 545–550), consistent with the recessive oncogene notion. Furthermore, rearrangements involving human chromosome 20 (to which the human RPTPα gene maps) have been linked to human lymphoid leukemia (Mitelman, F. (ed.) *Catalog of Chromosome Aberrations in Human Cancer*, A. Liss, New York).

Alternatively, RPTPα may act in a manner analogous to that proposed for the interaction between CD45 and c-lck (Oostergaard, H. L. et al., (1989) *Proc. Natl. Acad. Sci. USA* 86, 8959–8963; Mustelin, T. et al., (1989) *Proc. Natl. Acad. Sci. USA* 86, 6302–6306). According to this view, RPTPα would dephosphorylate negative regulatory sites in membrane-associated PTKs which are not receptors, and which are more widely expressed than lck (such as, for example, the tyr$^{527}$ site in pp60$^{c\text{-}src}$). Acting in this manner, RPTPα would be implicated in positive growth control and differentiation.

Although the inventors do not intend to be bound by any particular theory, the high interspecies conservation of the catalytic domains of the various RPTPs indicate an important role for these receptors in cell growth control.

10. EXAMPLE: ISOLATION AND CHARACTERIZATION OF HUMAN RPTP cDNA (See, also, Kaplan, R. et al., *Proc. Natl. Acad. Sci. USA* 87:7000–7004 (1990))

10.1. Materials

Restriction endonucleases and modifying enzymes were purchases from Boehringer-Mannheim or New England Biolabs. Taq DNA polymerase was from Perkin-Elmer/Cetus. The λgt11 forward and reverse primers (24-mers) used in the polymerase chain reactions as well as all sequencing primers, were synthesized on an automated DNA synthesizer (Applied Biosystems, model 380A) using either methoxy or β-cyanoethyl phosphoramidites (House, C., et al., *J. Biol. Chem.*, 262:772–777 (1987)). The λgt11 human brainstem cDNA library was obtained form the American Type Culture Collection (no. 37432). The LCA (CD45) clone used as a probe for screening the library was received from E. H. Fischer (University of Washington, Seattle). All sequencing reactions were performed using the Sequenase kit (United States Biochemical).

10.2. Methods

Approximately 300,000 plaques from a λgt11 cDNA library of 1-day-old human infant brainstem were screened on duplicate nitrocellulose filters under conditions of reduced stringency with a nick-translated LCA probe that spanned both conserved phosphatase domains (Charbonneau, H. et al., 1989, supra).

Hybridization was carried out at 55° C. overnight in a solution of 5×SSPE (SSPE is 10 mM NaH$_2$PO$_4$, pH 7.4/0.18 M NaCl/1 mM EDTA) containing 0.25% nonfat dry milk, 0.1% SDS, and $^{32}$P-labeled LCA probe at 10$^6$ cpm/ml. The filters were washed three times for 20 min at 55° C. in 2×SSPE/0.2% SDS and then processed for autoradiography. This screen yielded 79 duplicate positives; 12 of these, showing varying degrees of hybridization to the LCA probe, were plaque-purified by repetition screening with the same probe. The polymerase chain reaction (Saiki, R. K., et al., *Science*, 23d:1350–1354 (1985)) was then used to determine the sizes of the cDNA inserts. The DNA templates consisted of portions of the eluates from each pure plaque, heated at 75° C. for 15 min. to release the DNA. The templates were primed with the λgt11 forward and reverse primers. The reaction mixtures (0.1 ml) were prepared as described (Dionne, C. A. et al., Biotechniques 8:190–194 (1990)). Amplification was achieved by performing 30 cycles, each including 1.5 min of denaturation at 94° C., 2 min of annealing at 65° C., and 4 min of extension at 72° C., in an automated Perkin-Elmer/Cetus DNA thermal cycler. A portion of each sample (15 μl) was analyzed by electrophoresis through a 1% agarose gel containing ethidium bromide at 1 μg/ml (Sambrook et al., supra). DNA was prepared from the 4 largest clones by using LambdaSorb (Promega) and then digested with EcoRI. The fragments were subcloned separately into the EcoRI site of M13mp18 for sequencing. Nucleotide sequences were determined by the dideoxynucleotide chain-termination method (Sanger, F., et al., Proc. Natl. Acad. Sci. USA, 74:5463–5467 (1977)) using modified T7 polymerase (Tabor, S. et al., Proc. Natl. Acad. Sci. USA 84:4767–4771 (1987)).

All computer analyses of sequence data were performed on a Micro VAX II using programs written by IntelliGenetics. DNA sequences were analyzed and assembled using the GEL program. Hydrophobic analyses of proteins were based on the algorithm of Kyte and Doolittle (Kyte, J. et al., J. Mol. Biol. 157:105–132 (1982)), as implemented in the PEP program. Protein sequence alignments were done using the GENALIGN program (Sobel, E. et al., Nucleic Acids Res. 14:363–374 (1985); Karlin, S. et al., Mol. Biol. Evol. 1:357–370 (1984); Needleman, S. B. et al., J. Mol. Biol. 48:443–453 (1970)). Initial alignments were done using the Jimenez-Montano protein alphabet (Jimenez-Montano, M. et al., Proc. 7th Int'l. Biophysics Congress, 1981, Mexico City).

10.3. Results

In an effort to identify new members of the PTPase family, 300,000 plaques from a human infant brainstem cDNA library in λgt11 were screened under nonstringent conditions using a nick-translated LCA probe that spanned both conserved phosphatase domains. Four of the initial 79 duplicate positives were sequenced in the entirety. Two clones, 31-4 and 27-1, contained overlapping portions of the entire coding region of a human RPTP (huRPTP) that was designated RPTPα (FIGS. 4 and 8). The combined lengths of clones 31-4 and 27-1 equaled 3615 bp (FIG. 4A), encoding a protein of 802 amino acids (FIG. 4D) and containing an additional 695 bp and 510 bp, respectively, of 5' and 3' untranslated region. Two of the four clones contained portions of genes coding for two additional RPTPs which have been designated β and γ (FIG. 5). Like RPTPα, these two proteins contain typical hydrophobic transmembrane regions and distinct extracellular domains, indicating that they also represent separate RPTPs.

Thus, the nucleotide sequence of human RPTPα (SEQ ID NO:2) is shown in FIG. 8. The deduced amino acid sequence of the human RPTPα protein (SEQ ID NO:1) is shown in FIGS. 4D and 8.

The murine homologue of human RPTPΔ is described in Sections 6–9, above. A comparison of the mouse and human protein sequences (FIG. 4D) indicates that, with the exception of the extracellular domain, where some variability exists, only 5 residues are found to differ between the two proteins.

An examination of the structure of human RPTPα reveals the following features: a relatively short extracellular domain consisting of 150 residues that includes a hydrophobic signal peptide containing the only cysteine in this region. There are eight potential N-glycosylation sites, as well as a number of potential O-glycosylation sites (since this domain is rich in serine and threonine). The extracellular domains of RPTPα and the LCA and LAR molecules described by others appear to be structurally unrelated. Human RPTPα has a hydrophobic transmembrane region anchored on both sides by charged residues. This is followed by the two tandemly repeated conserved phosphatase domains of about 235 residues each, which are separated by 57 amino acids, typical of RPTPs such as LCA, LAR and the two Drosophila PTpases, DLAR and DPTP.

FIGS. 5A and 5B show the alignments of the amino acids within the first and second conserved phosphatase domains, respectively, of LCA and RPTPs α, β, and γ. It is readily apparent that among the four RPTPs, β and γ share the greatest sequence similarity. It was reported (Hunter, T. et al. supra) that among the sequences of the conserved phosphatase domains of PTPase 1B, LCA, LAR, DLAR and DPTP there are 29 invariant residues. While many of these residues are also present in both phosphatase domains of RPTPα, β, and γ, it is interesting that the second conserved phosphatase domains of both β and γ lack a number of these amino acids, including the two cysteines at positions 104 and 201 in phosphatase domain 2 of LCA (see FIG. 5B).

10.4. Discussion

The sequences of the conserved phosphatase domains of the three human RPTPs identified here (α, β, and γ) have been compared with one another as well as with those of LCA, LAR, and two soluble PTPases, placental phosphatase 1B and T-cell PTPase (Table IV). The two soluble enzymes have a sequence identity of 70%; however, when each is compared with the RPTPs (Phosphatase domains PD1 or PD2), this number drops to 29–42%. In all cases, the soluble PTPases showed a greater identity with PD1 than with PD2 of the RPTPS. RPTPα appears to be most related to LAR, since their PD1 sequences are 56% identical and their PD2 sequences are 52% identical. The conserved domains of RPTPβ and RPTPγ are most related to. each other, even more so than are the two soluble PTPases, β and γ being 75% identical in both PD1 and PD2. It is interesting that, in general, the sequence relationship between PD1 and PD2 within any RPTP appears to be no closer than that seen between different members of the family, i.e., the identities between PD1 and PD2 range from a high of 47% for LAR to a low of 29% for RPTP γ.

While the cytoplasmic domains of RPTPα, β, and γ are highly conserved, the extracellular domains of these receptors are unrelated to one another as well as to those of LAR and LCA. This suggests that each of these receptors has its own distinct ligand. It is likely that the binding of such ligands to the RPTPs plays a crucial role, together with growth factor receptors exhibiting PTKase activity, in the regulation of the level of tyrosine phosphorylation of targets proteins involved in signal transduction. The diversity of the RPTPs described herein reveals the existence of a multigene family. Greater understanding of structure-function relationships among these membrane receptors will provide important insights into the mechanisms involved in cell growth, differentiation, and oncogenesis.

TABLE IV

Identities Between Conserved Phosphatase Domains (Percent)

|  | PTPase 1B | T-cell PTPase | LCA PD1 | LCA PD2 | LAR PD1 | LAR PD2 | RPTPα PD1 | RPTPα PD2 | RPTPβ PD1 | RPTPβ PD2 | RPTPγ PD1 | RPTPγ PD2 |
|---|---|---|---|---|---|---|---|---|---|---|---|---|
| PTPase 1B | 100 | — | — | — | — | — | — | — | — | — | — | — |
| T-cell PTPase | 70 | 100 | — | — | — | — | — | — | — | — | — | — |
| LCA PD1 | 37 | 36 | 100 | — | — | — | — | — | — | — | — | — |
| LCA PD2 | 30 | 26 | 31 | 100 | — | — | — | — | — | — | — | — |
| LAR PD1 | 39 | 42 | 50 | 28 | 100 | — | — | — | — | — | — | — |
| LAR PD2 | 29 | 33 | 42 | 34 | 45 | 100 | — | — | — | — | — | — |
| RPTPα PD1 | 36 | 38 | 50 | 32 | 56 | 45 | 100 | — | — | — | — | — |
| RPTPα PD2 | 33 | 34 | 40 | 32 | 41 | 52 | 43 | 100 | — | — | — | — |
| RPTPβ PD1 | 35 | 39 | 41 | 31 | 33 | 41 | 47 | 33 | 100 | — | — | — |
| RPTPβ PD2 | 29 | 30 | 31 | 30 | 31 | 34 | 31 | 37 | 30 | 100 | — | — |
| RPTPγ PD1 | 35 | 34 | 32 | 29 | 39 | 36 | 34 | 32 | 75 | 27 | 100 | — |
| RPTPγ PD2 | 29 | 29 | 30 | 28 | 32 | 36 | 31 | 34 | 33 | 75 | 29 | 100 |

Alignments of the conserved phosphatase domains were carried out as described above. The regions compared are designated in FIG. 4C and FIG 5. PD = phosphatase domain.

11. EXAMPLE: EXPRESSION OF HUMAN RPTPα BY NORTHERN BLOT ANALYSIS

Samples containing either 20 μg of total RNA or 2 μg of poly(A)$^+$ RNA were resolved in a formaldehyde/agarose gel and transferred to nitrocellulose. RPTPα and β-actin probes were labeled by random priming (Sambrook et al., supra). Hybridizations and washes were carried out at 65° C. as described (Church, G., et al., Proc. Natl. Acad. Sci. USA, 81:1991–1995 (1984)). Blots hybridized with the RPTPα probe were exposed to XAR-2-x-ray film (Kodak) with an intensifying screen for 72 hr at −80° C. Results were obtained from the actin-probe blots after 15 hr under the same conditions.

RPTPα expression was examined in various cell lines and tissues (FIG. 6). The results indicate the presence of two major RNA transcripts of approximately 4.3 and 6.3 kb, respectively. The larger of the two species appears to be more prevalent in fetal tissues and in particularly prominent in the poly(A)$^+$ fetal liver sample, where there is also the highest relative amount of the 4.3-kb transcript. It is possible that the different expression of the two transcripts is developmentally regulated and/or a result of alternative splicing mechanisms, a feature seen with LCA (Ralph, S. J. supra). The adult brain shows relatively less expression of RPTPα. The results suggest that RPTPα is expressed to some degree throughout many tissues. Murine RPTPα was also shown to be expressed in many tissues and cell lines and most abundantly in brain and kidney (Sap, J., et al., Proc. Natl. Acad. Sci. USA, 87:6112–6116, (1990); see also Sections 8 and 9, above).

12. EXAMPLE: CHROMOSOME LOCALIZATION OF THE HUMAN RPTPα GENE

Isolation, propagation, and characterization of parental and somatic cell hybrids using in this study have been described (Durst, M. et al., Proc Natl. Acad. Sci. USA 84:1070–1074 (1987); Ku, D-H. et al., Somatic Cell Mol. Genet. 15:297–307 (1989); Juan, C-C. et al., Proc. Natl. Acad. Sci. USA 85:8910–8913 (1988)). Presence of specific human chromosomes or regions of chromosomes has been confirmed by DNA hybridization using probes for genes assigned to specific chromosome regions. Hybrid DNAs were digested with an excess of restriction endonuclease HindIII or EcoRI, sized by electrophoresis in 0.8% agarose gels, transferred to nylon filters, and hybridized as described (Durst et al., supra). The RPTPα probe consisted of the 3'-most 0.8 kilobases (kb) of clone 31-4 (see FIG. 4B).

DNAs from 17 rodent-human somatic cell hybrids carrying overlapping subsets of human chromosome regions representing the entire human genome were tested for presence of the human RPTPα locus by Southern blot analysis. The results (FIG. 7) show that presence of the human RPTPα locus in hybrid cells correlates only with presence of a partial human chromosome 20. The data also allow a regional localization for the RPTPα locus, since hybrids PB5-1 and AB3 are each missing a part of the long arm of chromosome 20 and yet retain the RPTPα locus. Thus, the human RPTPα gene maps to 20pter-20q12.

Murine homologues of all human genes which have been mapped to human chromosome 20 map to mouse chromosome 2 (Lalley, P. A. et al., Cytogenet. Cell Genet. 51:503–532 (1989)). This appears to be true for RPTPα as well (see Section 7, above). The long arm of human chromosome 20 is involved in translocation and deletions in myeloid disorders and neoplasms (Trent, J. M., et al., Cytogenet. Cell Genet., 51:533–562, (1989)). The human RPTPα locus may be specifically involved in deletion on 20q; in this case, it would strengthen the possibility of it being a tumor-suppressor gene or anti-oncogene. Similarly in mice, in the SJL/J strain, deletion of chromosome 2 appears to be involved in the development of radiation-induced myeloid leukemia (Trakhtenbrot, L., et al., Leukemia, 2:545–550, (1988)).

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for identifying a compound that modulates the phosphotyrosine phosphatase activity of a polypeptide, comprising:
   (a) incubating the compound with the polypeptide, wherein the polypeptide is in pure form, in a membrane preparation or in a whole cell;
   (b) measuring the phosphotyrosine phosphatase activity of the polypeptide; and
   (c) comparing the phosphotyrosine phosphatase activity in (b) to that of the polypeptide incubated without the compound, thereby determining whether said compound modulates the phosphotyrosine phosphatase activity of the polypeptide, wherein the polypeptide has phosphotyrosine phosphatase activity and comprises:
   i) the amino acid sequence SEQ ID NO:1;
   ii) an amino acid sequence encoded by a nucleic acid molecule that hybridizes at 42° C. in 50% formamide, 5×SSC, 25 mM KPO$_4$, 5×Denhardt's, 10 µg/ml salmon sperm DNA and 10% sulfate followed by washing at 58° C. in 0.1×SSC and 0.1% SDS to the complement of a nucleic acid molecule comprising the nucleotide sequence of SEQ ID NO: 2;
   iii) amino acid residues 1–500, 19–500, 151–500, 176–500, 265–500, 558–790 or 265–790 of SEQ ID NO: 1;
   iv) the amino acid sequence of SEQ ID NO: 3;
   v) an amino acid sequence encoded by a nucleic acid molecule that hybridizes at 42° C. in 50% formamide, 5×SSC, 25 mM KPO$_4$, 5×Denhardt's, 10 µ/ml salmon sperm DNA and 10% sulfate followed by washing at 58° C. in 0.1×SSC and 0.1% SDS to the complement of a nucleic acid molecule comprising the nucleotide sequence of SEQ ID NO:4; or
   vi) amino acid residues 1–486, 20–486, 143–486, 167–486, 259–486, 552–776 or 259–776 of SEQ ID NO:3.

2. The method of claim 1, wherein the polypeptide is a fusion polypeptide.

3. The method of claim 1, wherein the compound stimulates polypeptide phosphotyrosine phosphatase activity.

4. The method of claim 1, wherein the compound inhibits polypeptide phosphotyrosine phosphatase activity.

5. The method of claim 1, wherein the polypeptide comprises the amino acid sequence SEQ ID NO: 1.

6. The method of claim 1, wherein the polypeptide comprises an amino acid sequence encoded by a nucleic acid molecule that hybridizes at 42° C. in 50% formamide, 5×SSC, 25 mM KPO4, 5×Denhardt's, 10 µg/ml salmon sperm DNA and 10% sulfate followed by washing at 58° C.

in 0.1×SSC and 0.1% SDS to the complement of a nucleic acid molecule comprising the nucleotide sequence of SEQ ID NO: 2.

7. The method of claim 1, wherein the polypeptide comprises amino acid residues 1–500, 19–500, 151–500, 176–500, 265–500, 558–790 or 265–790 of SEQ ID NO: 1.

8. The method of claim 1, wherein the polypeptide comprises the amino acid sequence of SEQ ID NO: 3.

9. The method of claim 1, wherein the polypeptide comprises an amino acid sequence encoded by a nucleic acid molecule that hybridizes at 42° C. in 50% formamide, 5×SSC, 25 mM $KPO_4$, 5×Denhardt's, 10 µg/ml salmon sperm DNA and 10% sulfate followed by washing at 58° C. in 0.1×SSC and 0.1% SDS to the complement of a nucleic acid molecule comprising the nucleotide sequence of SEQ ID NO: 4.

10. The method of claim 1, wherein the polypeptide comprises amino acid residues 1–486, 20–486, 143–486, 167–486, 259–486, 552–776 or 259–776 of SEQ ID NO: 3.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 802 amino acids
      (B) TYPE: amino acid
      (D) TOPOLOGY: linear (ii) MOLECULE TYPE: protein (xi) SEQUENCE DESCRIPTION: SEQ ID NO:1:

```
Met Asp Ser Trp Phe Ile Leu Val Leu Leu Gly Ser Gly Leu Ile Cys
 1               5                  10                  15

Val Ser Ala Asn Asn Ala Thr Thr Val Ala Pro Ser Val Gly Ile Thr
             20                  25                  30

Arg Leu Ile Asn Ser Ser Thr Ala Glu Pro Val Lys Glu Glu Ala Lys
         35                  40                  45

Thr Ser Asn Pro Thr Ser Ser Leu Thr Ser Leu Ser Val Ala Pro Thr
     50                  55                  60

Phe Ser Pro Asn Ile Thr Leu Gly Pro Thr Tyr Leu Thr Thr Val Asn
65                  70                  75                  80

Ser Ser Asp Ser Asp Asn Gly Thr Thr Arg Thr Ala Ser Thr Asn Ser
                 85                  90                  95

Ile Gly Ile Thr Ile Ser Pro Asn Gly Thr Trp Leu Pro Asp Asn Gln
            100                 105                 110

Phe Thr Asp Ala Arg Thr Glu Pro Trp Glu Gly Asn Ser Ser Thr Ala
        115                 120                 125

Ala Thr Thr Pro Glu Thr Phe Pro Pro Ser Gly Asn Ser Asp Ser Lys
    130                 135                 140

Asp Arg Arg Asp Glu Thr Pro Ile Ile Ala Val Met Val Ala Leu Ser
145                 150                 155                 160

Ser Leu Leu Val Ile Val Phe Ile Ile Ile Val Leu Tyr Met Leu Arg
                165                 170                 175

Phe Lys Lys Tyr Lys Gln Ala Gly Ser His Ser Asn Ser Phe Arg Leu
            180                 185                 190

Ser Asn Gly Arg Thr Glu Asp Val Glu Pro Gln Ser Val Pro Leu Leu
        195                 200                 205

Ala Arg Ser Pro Ser Thr Asn Arg Lys Tyr Pro Pro Leu Pro Val Asp
    210                 215                 220

Lys Leu Glu Glu Glu Ile Asn Arg Arg Met Ala Asp Asp Asn Lys Leu
225                 230                 235                 240

Phe Arg Glu Glu Phe Asn Ala Leu Pro Ala Cys Pro Ile Gln Ala Thr
                245                 250                 255

Cys Glu Ala Ala Ser Lys Glu Glu Asn Lys Glu Lys Asn Arg Tyr Val
            260                 265                 270

Asn Ile Leu Pro Tyr Asp His Ser Arg Val His Leu Thr Pro Val Glu
        275                 280                 285

Gly Val Pro Asp Ser Asp Tyr Ile Asn Ala Ser Phe Ile Asn Gly Tyr
    290                 295                 300

Gln Glu Lys Asn Lys Phe Ile Ala Ala Gln Gly Pro Lys Glu Glu Thr
305                 310                 315                 320
```

-continued

```
Val Asn Asp Phe Trp Arg Met Ile Trp Glu Gln Asn Thr Ala Thr Ile
                325                 330                 335

Val Met Val Thr Asn Leu Lys Glu Arg Lys Glu Cys Lys Cys Ala Gln
            340                 345                 350

Tyr Trp Pro Asp Gln Gly Cys Trp Thr Tyr Gly Asn Ile Arg Val Ser
        355                 360                 365

Val Glu Asp Val Thr Val Leu Val Asp Tyr Thr Val Arg Lys Phe Cys
    370                 375                 380

Ile Gln Gln Val Gly Asp Met Thr Asn Arg Lys Pro Gln Arg Leu Ile
385                 390                 395                 400

Thr Gln Phe His Phe Thr Ser Trp Pro Asp Phe Gly Val Pro Phe Thr
                405                 410                 415

Pro Ile Gly Met Leu Lys Phe Leu Lys Lys Val Lys Ala Cys Asn Pro
            420                 425                 430

Gln Tyr Ala Gly Ala Ile Val Val His Cys Ser Ala Gly Val Gly Arg
        435                 440                 445

Thr Gly Thr Phe Val Val Ile Asp Ala Met Leu Asp Met Met His Thr
    450                 455                 460

Glu Arg Lys Val Asp Val Tyr Gly Phe Val Ser Arg Ile Arg Ala Gln
465                 470                 475                 480

Arg Cys Gln Met Val Gln Thr Asp Met Gln Tyr Val Phe Ile Tyr Gln
                485                 490                 495

Ala Leu Leu Glu His Tyr Leu Tyr Gly Asp Thr Glu Leu Glu Val Thr
            500                 505                 510

Ser Leu Glu Thr His Leu Gln Lys Ile Tyr Asn Lys Ile Pro Gly Thr
        515                 520                 525

Ser Asn Asn Gly Leu Glu Glu Phe Lys Lys Leu Thr Ser Ile Lys
    530                 535                 540

Ile Gln Asn Asp Lys Met Arg Thr Gly Asn Leu Pro Ala Asn Met Lys
545                 550                 555                 560

Lys Asn Arg Val Leu Gln Ile Ile Pro Tyr Glu Phe Asn Arg Val Ile
                565                 570                 575

Ile Pro Val Lys Arg Gly Glu Glu Asn Thr Asp Tyr Val Asn Ala Ser
            580                 585                 590

Phe Ile Asp Gly Tyr Arg Gln Lys Asp Ser Tyr Ile Ala Ser Gln Gly
        595                 600                 605

Pro Leu Leu His Thr Ile Glu Asp Phe Trp Arg Met Ile Trp Glu Trp
    610                 615                 620

Lys Ser Cys Ser Ile Val Met Leu Thr Glu Leu Glu Glu Arg Gly Gln
625                 630                 635                 640

Glu Lys Cys Ala Gln Tyr Trp Pro Ser Asp Gly Leu Val Ser Tyr Gly
                645                 650                 655

Asp Ile Thr Val Glu Leu Lys Lys Glu Glu Cys Glu Ser Tyr Thr
            660                 665                 670

Val Arg Asp Leu Leu Val Thr Asn Thr Arg Glu Asn Lys Ser Arg Gln
        675                 680                 685

Ile Arg Gln Phe His Phe His Gly Trp Pro Glu Val Gly Ile Pro Ser
    690                 695                 700

Asp Gly Lys Gly Met Ile Ser Ile Ile Ala Ala Val Gln Lys Gln Gln
705                 710                 715                 720

Gln Gln Ser Gly Asn His Pro Ile Thr Val His Cys Ser Ala Gly Ala
                725                 730                 735

Gly Arg Thr Gly Thr Phe Cys Ala Leu Ser Thr Val Leu Glu Arg Val
```

```
               740             745             750
Lys Ala Glu Gly Ile Leu Asp Val Phe Gln Thr Val Lys Ser Leu Arg
        755             760             765

Leu Gln Arg Pro His Met Val Gln Thr Leu Glu Gln Tyr Glu Phe Cys
        770             775             780

Tyr Lys Val Val Gln Glu Tyr Ile Asp Ala Phe Ser Asp Tyr Ala Asn
785             790             795             800

Phe Lys (2) INFORMATION FOR SEQ ID NO:2:

(i) SEQUENCE CHARACTERISTICS:
        (A) LENGTH: 2409 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:2:
```

| | | | | | |
|---|---|---|---|---|---|
| ATGGATTCCT | GGTTCATTCT | TGTTCTGCTC | GGCAGTGGTC | TGATATGTGT | CAGTGCCAAC | 60 |
| AATGCTACCA | CAGTTGCACC | TTCTGTAGGA | ATTACAAGAT | TAATTAACTC | ATCAACGGCA | 120 |
| GAACCAGTTA | AGAAGAGGC | CAAAACTTCA | AATCCAACTT | CTTCACTAAC | TTCTCTTTCT | 180 |
| GTGGCACCAA | CATTCAGCCC | AAATATAACT | CTGGGACCCA | CCTATTTAAC | CACTGTCAAT | 240 |
| TCTTCAGACT | CTGACAATGG | GACCACAAGA | ACAGCAAGCA | CCAATTCTAT | AGGCATTACA | 300 |
| ATTTCACCAA | ATGGAACGTG | GCTTCCAGAT | AACCAGTTCA | CGGATGCCAG | AACAGAACCC | 360 |
| TGGGAGGGA | ATTCCAGCAC | CGCAGCAACC | ACTCCAGAAA | CTTTCCCTCC | TTCAGGTAAT | 420 |
| TCTGACTCGA | AGGACAGAAG | AGATGAGACA | CCAATTATTG | CGGTGATGGT | GGCCCTGTCC | 480 |
| TCTCTGCTAG | TGATCGTGTT | TATTATCATA | GTTTTGTACA | TGTTAAGGTT | TAAGAAATAC | 540 |
| AAGCAAGCTG | GGAGCCATTC | CAATTCTTTC | CGCTTATCCA | ACGGCCGCAC | TGAGGATGTG | 600 |
| GAGCCCCAGA | GTGTGCCACT | TCTGGCCAGA | TCCCCAAGCA | CCAACAGGAA | ATACCCACCC | 660 |
| CTGCCCGTGG | ACAAGCTGGA | AGAGGAAATT | AACCGGAGAA | TGGCAGACGA | CAATAAGCTC | 720 |
| TTCAGGGAGG | AATTCAACGC | TCTCCCTGCA | TGTCCTATCC | AGGCCACCTG | TGAGGCTGCT | 780 |
| TCCAAGGAGG | AAAACAAGGA | AAAAAATCGA | TATGTAAACA | TCTTGCCTTA | TGACCACTCT | 840 |
| AGAGTCCACC | TGACACCGGT | TGAAGGGGTT | CCAGATTCTG | ATTACATCAA | TGCTTCATTC | 900 |
| ATCAACGGTT | ACCAAGAAAA | GAACAAATTC | ATTGCTGCAC | AAGGACCAAA | AGAAGAAACG | 960 |
| GTGAATGATT | TCTGGCGGAT | GATCTGGGAA | CAAAACACAG | CCACCATCGT | CATGGTTACC | 1020 |
| AACCTGAAGG | AGAGAAAGGA | GTGCAAGTGC | GCCCAGTACT | GGCCAGACCA | AGGCTGCTGG | 1080 |
| ACCTATGGGA | ATATTCGGGT | GTCTGTAGAG | GATGTGACTG | TCCTGGTGGA | CTACACAGTA | 1140 |
| CGGAAGTTCT | GCATCCAGCA | GGTGGGCGAC | ATGACCAACA | GAAAGCCACA | GCGCCTCATC | 1200 |
| ACTCAGTTCC | ACTTTACCAG | CTGGCCAGAC | TTTGGGGTGC | CTTTTACCCC | GATCGGCATG | 1260 |
| CTCAAGTTCC | TCAAGAAGGT | GAAGGCCTGT | AACCCTCAGT | ATGCAGGGGC | CATCGTGGTC | 1320 |
| CACTGCAGTG | CAGGTGTAGG | GCGTACAGGT | ACCTTTGTCG | TCATTGATGC | CATGCTGGAC | 1380 |
| ATGATGCATA | CAGAACGGAA | GGTGGACGTG | TATGGCTTTG | TGAGCCGGAT | CCGGGCACAG | 1440 |
| CGCTGCCAGA | TGGTGCAAAC | CGATATGCAG | TATGTCTTCA | TATACCAAGC | CCTTCTGGAG | 1500 |
| CATTATCTCT | ATGGAGATAC | AGAACTGGAA | GTGACCTCTC | TAGAAACCCA | CCTGCAGAAA | 1560 |
| ATTTACAACA | AAATCCCAGG | GACCAGCAAC | AATGGATTAG | AGGAGGAGTT | TAAGAAGTTA | 1620 |

-continued

```
ACATCAATCA AAATCCAGAA TGACAAGATG CGGACTGGAA ACCTTCCAGC CAACATGAAG      1680

AAGAACCGTG TTTTACAGAT CATTCCATAT GAATTCAACA GAGTGATCAT TCCAGTTAAG      1740

CGGGGCGAAG AGAATACAGA CTATGTGAAC GCATCCTTTA TTGATGGCTA CCGGCAGAAG      1800

GACTCCTATA TCGCCAGCCA GGGCCCTCTT CTCCACACAA TTGAGGACTT CTGGCGAATG      1860

ATCTGGGAGT GGAAATCCTG CTCTATCGTG ATGCTAACAG AACTGGAGGA GAGAGGCCAG      1920

GAGAAGTGTG CCCAGTACTG GCCATCTGAT GGACTGGTGT CCTATGGAGA TATTACAGTG      1980

GAACTGAAGA AGGAGGAGGA ATGTGAGAGC TACACCGTCC GAGACCTCCT GGTCACCAAC      2040

ACCAGGGAGA ATAAGAGCCG GCAGATCCGG CAGTTCCACT TCCATGGCTG GCCTGAAGTG      2100

GGCATCCCCA GTGACGGAAA GGGCATGATC AGCATCATCG CCGCCGTGCA GAAGCAGCAG      2160

CAGCAGTCAG GGAACCACCC CATCACCGTG CACTGCAGCG CCGGGGCAGG AAGGACGGGG      2220

ACCTTCTGTG CCCTGAGCAC CGTCCTGGAG CGTGTGAAAG CAGAGGGGAT TTTGGATGTC      2280

TTCCAGACTG TCAAGAGCCT GCGGCTACAG AGGCCACACA TGGTCCAGAC ACTGGAACAG      2340

TATGAGTTCT GCTACAAGGT GGTGCAGGAG TATATTGATG CATTCTCAGA TTATGCCAAC      2400

TTCAAGTAA                                                             2409
```

(2) INFORMATION FOR SEQ ID NO:3:

(i) SEQUENCE CHARACTERISTICS:
        (A) LENGTH: 793 amino acids
        (B) TYPE: amino acid
        (D) TOPOLOGY: linear (ii) MOLECULE TYPE: protein (xi) SEQUENCE DESCRIPTION: SEQ ID NO:3:

```
Met Asp Ser Trp Phe Ile Leu Val Leu Phe Gly Ser Gly Leu Ile His
  1               5                  10                  15

Val Ser Ala Asn Asn Ala Thr Thr Val Ser Pro Ser Leu Gly Thr Thr
                 20                  25                  30

Arg Leu Ile Lys Thr Ser Thr Thr Glu Leu Ala Lys Glu Glu Asn Lys
             35                  40                  45

Thr Ser Asn Ser Thr Ser Ser Val Ile Ser Leu Ser Val Ala Pro Thr
         50                  55                  60

Phe Ser Pro Asn Leu Thr Leu Glu Pro Thr Tyr Val Thr Thr Val Asn
 65                  70                  75                  80

Ser Ser His Ser Asp Asn Gly Thr Arg Arg Ala Ala Ser Thr Glu Ser
                 85                  90                  95

Gly Gly Thr Thr Ile Ser Pro Asn Gly Ser Trp Leu Ile Glu Asn Gln
                100                 105                 110

Phe Thr Asp Ala Ile Thr Glu Pro Trp Glu Gly Asn Ser Ser Thr Ala
            115                 120                 125

Ala Thr Pro Glu Thr Phe Pro Pro Ala Asp Glu Thr Pro Ile Ile
        130                 135                 140

Ala Val Met Val Ala Leu Ser Ser Leu Leu Val Ile Val Phe Ile Ile
145                 150                 155                 160

Ile Val Leu Tyr Met Leu Arg Phe Lys Lys Tyr Lys Gln Ala Gly Ser
                165                 170                 175

His Ser Asn Ser Phe Arg Leu Ser Asn Gly Arg Thr Glu Asp Val Glu
            180                 185                 190

Pro Gln Ser Val Pro Leu Leu Ala Arg Ser Pro Ser Thr Asn Arg Lys
        195                 200                 205
```

-continued

```
Tyr Pro Pro Leu Pro Val Asp Lys Leu Glu Glu Ile Asn Arg Arg
    210                 215                 220

Met Ala Asp Asp Asn Lys Leu Phe Arg Glu Glu Phe Asn Ala Leu Pro
225                 230                 235                 240

Ala Cys Pro Ile Gln Ala Thr Cys Glu Ala Ala Ser Lys Glu Glu Asn
                245                 250                 255

Lys Glu Lys Asn Arg Tyr Val Asn Ile Leu Pro Tyr Asp His Ser Arg
                260                 265                 270

Val His Leu Thr Pro Val Glu Gly Val Pro Asp Ser Asp Tyr Ile Asn
        275                 280                 285

Ala Ser Phe Ile Asn Gly Tyr Gln Glu Lys Asn Lys Phe Ile Ala Ala
        290                 295                 300

Gln Gly Pro Lys Glu Glu Thr Val Asn Asp Phe Trp Arg Met Ile Trp
305                 310                 315                 320

Glu Gln Asn Thr Ala Thr Ile Val Met Val Thr Asn Leu Lys Glu Arg
                325                 330                 335

Lys Glu Cys Lys Cys Ala Gln Tyr Trp Pro Asp Gln Gly Cys Trp Thr
                340                 345                 350

Tyr Gly Asn Val Arg Val Ser Val Glu Asp Val Thr Val Leu Val Asp
        355                 360                 365

Tyr Thr Val Arg Lys Phe Ser Ile Gln Gln Val Gly Asp Val Thr Asn
370                 375                 380

Arg Lys Pro Gln Arg Leu Ile Thr Gln Phe His Phe Thr Ser Trp Pro
385                 390                 395                 400

Asp Phe Gly Val Pro Phe Thr Pro Ile Gly Met Leu Lys Phe Leu Lys
                405                 410                 415

Lys Val Lys Ala Cys Asn Pro Gln Tyr Ala Gly Ala Ile Val Val His
                420                 425                 430

Cys Ser Ala Gly Val Gly Arg Thr Gly Thr Phe Val Val Ile Asp Ala
        435                 440                 445

Met Leu Asp Met Met His Ser Glu Arg Lys Val Asp Val Tyr Gly Phe
450                 455                 460

Val Ser Arg Ile Arg Ala Gln Arg Cys Gln Met Val Gln Thr Asp Met
465                 470                 475                 480

Gln Tyr Val Phe Ile Tyr Gln Ala Leu Leu Glu His Tyr Leu Tyr Gly
                485                 490                 495

Asp Thr Glu Leu Glu Val Thr Ser Leu Glu Thr His Leu Gln Lys Ile
                500                 505                 510

Tyr Asn Lys Ile Pro Gly Thr Ser Asn Asn Gly Leu Glu Glu Glu Phe
                515                 520                 525

Lys Lys Leu Thr Ser Ile Lys Ile Gln Asn Asp Lys Met Arg Thr Gly
        530                 535                 540

Asn Leu Pro Ala Asn Met Lys Lys Asn Arg Val Leu Gln Ile Ile Pro
545                 550                 555                 560

Tyr Glu Phe Asn Arg Val Ile Ile Pro Val Lys Arg Gly Glu Glu Asn
                565                 570                 575

Thr Asp Tyr Val Asn Ala Ser Phe Ile Asp Gly Tyr Arg Gln Lys Asp
                580                 585                 590

Ser Tyr Ile Ala Ser Gln Gly Pro Leu Leu His Thr Ile Glu Asp Phe
        595                 600                 605

Trp Arg Met Ile Trp Glu Trp Lys Ser Cys Ser Ile Val Met Leu Thr
610                 615                 620
```

```
Glu Leu Glu Glu Arg Gly Gln Glu Lys Cys Ala Gln Tyr Trp Pro Ser
625                 630                 635                 640

Asp Gly Leu Val Ser Tyr Gly Asp Ile Thr Val Glu Leu Lys Lys Glu
                645                 650                 655

Glu Glu Cys Glu Ser Tyr Thr Val Arg Asp Leu Leu Val Thr Asn Thr
            660                 665                 670

Arg Glu Asn Lys Ser Arg Gln Ile Arg Gln Phe His Phe His Gly Trp
        675                 680                 685

Pro Glu Val Gly Ile Pro Ser Asp Gly Lys Gly Met Ile Asn Ile Ile
    690                 695                 700

Ala Ala Val Gln Lys Gln Gln Gln Ser Gly Asn His Pro Ile Thr
705                 710                 715                 720

Val His Cys Ser Ala Gly Ala Gly Arg Thr Gly Thr Phe Cys Ala Leu
                725                 730                 735

Ser Thr Val Leu Glu Arg Val Lys Ala Glu Gly Ile Leu Asp Val Phe
            740                 745                 750

Gln Thr Val Lys Ser Leu Arg Leu Gln Arg Pro His Met Val Gln Thr
        755                 760                 765

Leu Glu Gln Tyr Glu Phe Cys Tyr Lys Val Val Gln Glu Tyr Ile Asp
    770                 775                 780

Ala Phe Ser Asp Tyr Ala Asn Phe Lys
785                 790

(2) INFORMATION FOR SEQ ID NO:4:

(i) SEQUENCE CHARACTERISTICS:
        (A) LENGTH: 2872 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:4:

GAATTCCGGC GAGTGAGGCG CTGACAGGGA CTCGCGGGGG CATCTTGCAC AGACCCCTGG        60

ACCACGCCGC CATCGCAGCC TCCAGCCCAG TCCTCTCTCT GCCGCTTCTC CTCGCCATGG       120

AGGCCGCCGA CCGCCGTCCG CGGGCTTCGA GCAGCGGACC GGGCCGGGCT GACCCCATGT       180

GGGCCGAGAG CCCGGTCCTG AGGCGGAGCT GCCGTGCGCG TCCCCCGCGG TCCCGCCCCA       240

GCGCCGGGCT CGGTCAGCAT GGATTCCTGG TTCATTCTTG TCCTGTTTGG CAGTGGTCTA       300

ATACATGTTA GTGCCAACAA TGCTACTACA GTTTCACCTT CTTTAGGAAC GACAAGATTA       360

ATTAAAACAT CAACAACAGA ATTGGCTAAG AAGAGAATA AAACCTCAAA TTCAACCTCT        420

TCAGTAATTT CTCTTTCTGT GGCACCAACA TTCAGCCCAA ACTGACTCT GGAGCCCACC        480

TATGTGACTA CTGTTAATTC TTCACACTCT GACAATGGGA CCAGGAGGGC AGCCAGCACG      540

GAATCTGGAG GCACTACCAT TTCCCCGAAC GGAAGCTGGC TTATTGAGAA CCAGTTCACG       600

GATGCCATAA CAGAACCCTG GGAGGGGAAC TCCAGCACTG CAGCAACCAC TCCAGAAACC       660

TTCCCCCCGG CAGATGAGAC ACCAATTATT GCGGTGATGG TGGCCCTGTC CTCTCTGCTA       720

GTAATCGTGT TTATTATCAT AGTTCTGTAC ATGTTAAGGT TTAAGAAATA CAAGCAAGCT       780

GGGAGTCATT CCAACTCTTT CCGCCTGTCA AATGGCCGCA CGGAGGATGT GGAGCCCCAA       840

AGTGTACCAC TTCTGGCCAG GTCCCCGAGC ACCAACAGGA AGTACCCACC ACTGCCTGTG       900

GACAAGCTGG AAGAGGAGAT TAACCGGAGA ATGGCTGATG ACAATAAGCT CTTCAGAGAA       960

GAATTCAACG CTCTCCCTGC TTGTCCTATC CAGGCCACCT GTGAGGCTGC CTCCAAGGAA      1020
```

```
GAAAACAAGG AAAAAAACCG CTATGTAAAC ATCCTGCCCT ATGACCACTC TAGAGTGCAC    1080

CTGACACCTG TTGAAGGGGT CCCAGATTCT GATTACATCA ACGCTTCATT CATTAATGGC    1140

TACCAGGAAA AGAACAAATT CATCGCTGCA CAAGGACCAA AGAAGAAAC AGTGAATGAC     1200

TTCTGGAGAA TGTATATGGGA ACAAAACACA GCTACTATTG TCATGGTGAC CAACCTGAAG   1260

GAGAGAAAGG AGTGTAAATG TGCCCAATAC TGGCCAGACC AAGGCTGCTG GACCTATGGG    1320

AATGTCCGTG TGTCTGTCGA GGATGTGACT GTTCTGGTGG ACTACACAGT ACGGAAATTC    1380

TCGATCCAGC AGGTGGGCGA CGTGACCAAC AGGAAACCAC AGCGCCTCAT CACTCAGTTC    1440

CACTTCACCA GCTGGCCAGA CTTTGGGGTG CCTTTCACCC CAATTGGCAT GCTCAAGTTC    1500

CTCAAGAAGG TGAAGGCCTG TAACCCTCAG TACGCAGGGG CTATCGTGGT CCACTGCAGT    1560

GCAGGTGTAG GCGCACTGG CACCTTTGTT GTCATCGATG CCATGCTGGA CATGATGCAT    1620

TCGGAGCGCA AAGTGGATGT ATATGGGTTT GTGAGCCGGA TCCGGGCCCA GCGCTGCCAG    1680

ATGGTACAGA CAGACATGCA GTACGTCTTC ATATACCAGG CCCTTCTGGA GCATTATCTG    1740

TATGGGGACA CAGAACTGGA AGTGACTTCT CTAGAAACCC ACCTACAAAA AATTTATAAC    1800

AAGATCCCAG GGACTAGCAA CAACGGGTTA GAGGAGGAGT TTAAGAAATT AACTTCAATC    1860

AAAATCCAGA ATGACAAGAT GCGCACGGGA AACCTTCCAG CCAACATGAA GAAGAACCGG    1920

GTTTTACAGA TCATTCCATA TGAATTTAAC AGAGTGATCA TTCCAGTCAA CGAGGCGAA    1980

GAGAACACAG ACTATGTGAA CGCATCCTTC ATTGATGGAT ACCGGCAGAA AGACTCCTAC    2040

ATTGCCAGCC AGGGCCCTCT TCTCCACACG ATTGAGGACT TCTGGCGAAT GATCTGGGAG    2100

TGGAAGTCCT GTTCTATCGT AATGCTGACA GAACTGGAAG AGAGAGGCCA GGAGAAGTGT    2160

GCCCAGTACT GGCCATCTGA TGGCCTGGTG TCCTACGGAG ACATCACAGT TGAGCTGAAG    2220

AAGGAGGAGG AATGTGAAAG CTACACTGTC CGAGACCTCC TGGTCACCAA CACCAGGGAG    2280

AACAAGAGTC GGCAAATCCG GCAGTTCCAC TTCCACGGCT GGCCTGAGGT GGGCATCCCC    2340

AGCGACGGCA AGGGCATGAT CAACATCATT GCAGCAGTGC AGAAGCAGCA GCAGCAGTCG    2400

GGGAACCATC CCATCACTGT GCACTGCAGT GCCGGGCAG GACGGACAGG AACCTTCTGT    2460

GCCTTGAGCA CAGTCCTGGA ACGTGTGAAA GCAGAAGGAA TTTTAGATGT CTTCCAAACT    2520

GTCAAGAGCC TGCGGCTGCA GAGGCCACAC ATGGTCCAGA CACTGGAACA GTATGAATTC    2580

TGCTACAAGG TGGTACAGGA ATACATTGAC GCCTTTTCAG ATTATGCCAA CTTCAAGTGA    2640

CAGGTGACAA GGCCCACAGA CAGGAGAATT GCCTTTAATA TTTTGTAATA TTCTGTTTTT    2700

GTTAATATAC CCAAAATTGT ATATATCTTA TAACTGTTTT AGAAATGGCA CATAGGCTTC    2760

TATTACCTGT TAGATGGAGA TTTTGTATGT AAATGTGTTA GCACTGATAG TCCTTTTCCA    2820

GTGTTTTATT GGGAAATTAA TAGTGTGATA TTTGGGTTGA TATAATGAAT TC            2872
```

(2) INFORMATION FOR SEQ ID NO:5:

(i) SEQUENCE CHARACTERISTICS:
        (A) LENGTH: 235 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:5:

```
Asn Gln Asn Lys Asn Arg Tyr Val Asp Ile Leu Pro Tyr Asp Tyr Asn
1               5                  10                  15
```

```
Arg Val Glu Leu Ser Glu Ile Asn Gly Asp Ala Gly Ser Asn Tyr Ile
         20                  25                  30

Asn Ala Ser Tyr Ile Asp Gly Phe Lys Glu Pro Arg Lys Tyr Ile Ala
             35                  40                  45

Ala Gln Gly Pro Arg Asp Glu Thr Val Asp Asp Phe Trp Arg Met Ile
 50                  55                  60

Trp Glu Gln Lys Ala Thr Val Ile Val Met Val Thr Arg Cys Glu Glu
 65                  70                  75                  80

Gly Asn Arg Asn Lys Cys Ala Glu Tyr Trp Pro Ser Met Glu Glu Gly
                 85                  90                  95

Thr Arg Ala Phe Gly Asp Val Val Lys Ile Asn Gln His Lys Arg
                100                 105                 110

Cys Pro Asp Tyr Ile Ile Gln Lys Leu Asn Ile Val Asn Lys Lys Glu
            115                 120                 125

Lys Ala Thr Gly Arg Glu Val Thr His Ile Gln Phe Thr Ser Trp Pro
130                 135                 140

Asp His Gly Val Pro Glu Asp Pro His Leu Leu Leu Lys Leu Arg Arg
145                 150                 155                 160

Arg Val Asn Ala Phe Ser Asn Phe Phe Ser Gly Pro Ile Val His
                165                 170                 175

Cys Ser Ala Gly Val Gly Arg Thr Gly Thr Tyr Ile Gly Ile Asp Ala
            180                 185                 190

Met Leu Glu Gly Leu Glu Ala Glu Asn Lys Val Asp Val Tyr Gly Tyr
        195                 200                 205

Val Val Lys Leu Arg Arg Gln Arg Cys Leu Met Val Gln Val Glu Ala
        210                 215                 220

Gln Tyr Ile Leu Ile His Gln Ala Leu Val Glu
225                 230                 235

(2) INFORMATION FOR SEQ ID NO:6:

(i) SEQUENCE CHARACTERISTICS:
        (A) LENGTH: 236 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:6:

Asn Lys Glu Lys Asn Arg Tyr Val Asn Ile Leu Pro Tyr Asp His Ser
 1               5                  10                  15

Arg Val His Leu Thr Pro Val Glu Gly Val Pro Asp Ser Asp Tyr Ile
            20                  25                  30

Asn Ala Ser Phe Ile Asn Gly Tyr Gln Glu Lys Asn Lys Phe Ile Ala
            35                  40                  45

Ala Gln Gly Pro Lys Glu Glu Thr Val Asn Asp Phe Trp Arg Met Ile
 50                  55                  60

Trp Glu Gln Asn Thr Ala Thr Ile Val Met Val Thr Asn Leu Lys Glu
 65                  70                  75                  80

Arg Lys Glu Cys Lys Cys Ala Gln Tyr Trp Pro Asp Gln Gly Glu Trp
                 85                  90                  95

Thr Tyr Gly Asn Ile Arg Val Ser Val Glu Asp Val Thr Val Leu Val
            100                 105                 110

Asp Tyr Thr Val Arg Lys Phe Cys Ile Gln Gln Val Gly Asp Met Thr
            115                 120                 125
```

```
Asn Arg Lys Pro Gln Arg Leu Ile Thr Gln Phe His Phe Thr Ser Trp
    130                 135                 140

Pro Asp Phe Gly Val Pro Phe Thr Pro Ile Gly Met Leu Lys Phe Leu
145                 150                 155                 160

Lys Lys Val Lys Ala Cys Asn Pro Gln Tyr Ala Gly Ala Ile Val Val
                165                 170                 175

His Cys Ser Ala Gly Val Gly Arg Thr Gly Thr Phe Val Val Ile Asp
            180                 185                 190

Ala Met Leu Asp Met Met His Thr Glu Arg Lys Val Asp Val Tyr Gly
        195                 200                 205

Phe Val Ser Arg Ile Arg Ala Gln Arg Cys Gln Met Val Gln Thr Asp
    210                 215                 220

Met Gln Tyr Val Phe Ile Tyr Gln Ala Leu Leu Glu
225                 230                 235

(2) INFORMATION FOR SEQ ID NO:7:

(i) SEQUENCE CHARACTERISTICS:
        (A) LENGTH: 242 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:7:

Asn Lys His Lys Asn Arg Tyr Ile Asn Ile Val Ala Tyr Asp His Ser
1               5                   10                  15

Arg Val Lys Leu Ala Gln Leu Ala Glu Lys Asp Gly Lys Leu Thr Asp
                20                  25                  30

Tyr Ile Asn Ala Asn Tyr Val Asp Gly Tyr Asn Arg Pro Lys Ala Tyr
            35                  40                  45

Ile Ala Ala Gln Gly Pro Leu Lys Ser Thr Ala Glu Asp Phe Trp Arg
        50                  55                  60

Met Ile Trp Glu His Asn Val Glu Val Ile Val Met Ile Thr Asn Leu
65                  70                  75                  80

Val Glu Lys Gly Arg Arg Lys Cys Asp Gln Tyr Trp Pro Ala Asp Gly
                85                  90                  95

Ser Glu Glu Tyr Gly Asn Phe Leu Val Thr Gln Lys Ser Val Gln Val
                100                 105                 110

Leu Ala Tyr Tyr Thr Val Arg Asn Phe Thr Leu Arg Asn Thr Lys Ile
            115                 120                 125

Lys Lys Gly Ser Gln Lys Gly Arg Pro Ser Gly Arg Val Val Thr Gln
        130                 135                 140

Tyr His Tyr Thr Gln Trp Pro Asp Met Gly Val Pro Glu Tyr Ser Leu
145                 150                 155                 160

Pro Val Leu Thr Phe Val Arg Lys Ala Ala Tyr Ala Lys Arg His Ala
                165                 170                 175

Val Gly Pro Val Val His Cys Ser Ala Gly Val Gly Arg Thr Gly Thr
            180                 185                 190

Thr Tyr Ile Val Leu Asp Ser Met Leu Gln Gln Ile Gln His Glu Gly
        195                 200                 205

Thr Val Asn Ile Phe Gly Phe Leu Lys His Ile Arg Ser Gln Arg Asn
    210                 215                 220

Tyr Leu Val Gln Thr Glu Glu Gln Tyr Val Phe Ile His Asp Thr Leu
225                 230                 235                 240
```

Val Glu (2) INFORMATION FOR SEQ ID NO:8:

(i) SEQUENCE CHARACTERISTICS:
        (A) LENGTH: 245 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:8:

```
Asn Lys His Lys Asn Arg Tyr Ile Asn Ile Leu Ala Tyr Asp His Ser
 1               5                  10                  15
Arg Val Lys Leu Arg Pro Leu Pro Gly Lys Asp Ser Lys His Ser Asp
                20                  25                  30
Tyr Ile Asn Ala Asn Tyr Val Asp Gly Tyr Asn Lys Ala Lys Ala Tyr
            35                  40                  45
Ile Ala Thr Gln Gly Pro Leu Lys Ser Thr Phe Glu Asp Phe Trp Arg
        50                  55                  60
Met Ile Trp Glu Gln Asn Thr Gly Ile Ile Val Met Ile Thr Asn Leu
65                  70                  75                  80
Val Glu Lys Gly Arg Arg Lys Cys Asp Gln Tyr Trp Pro Thr Glu Asn
                85                  90                  95
Ser Glu Glu Tyr Gly Asn Ile Ile Val Thr Leu Lys Ser Thr Lys Ile
            100                 105                 110
His Ala Cys Tyr Thr Val Arg Arg Phe Ser Ile Arg Asn Thr Lys Val
        115                 120                 125
Lys Lys Gly Gln Lys Gly Asn Pro Lys Gly Arg Gln Asn Glu Arg Val
        130                 135                 140
Val Ile Gln Tyr His Tyr Thr Gln Trp Pro Asp Met Gly Val Pro Glu
145                 150                 155                 160
Tyr Ala Leu Pro Val Leu Thr Phe Val Arg Arg Ser Ser Ala Ala Arg
                165                 170                 175
Met Pro Glu Thr Gly Pro Val Leu Val His Cys Ser Ala Gly Val Gly
            180                 185                 190
Arg Thr Gly Thr Tyr Ile Val Ile Asp Ser Met Leu Gln Gln Ile Lys
        195                 200                 205
Asp Lys Ser Thr Val Asn Val Leu Gly Phe Leu Lys His Ile Arg Thr
        210                 215                 220
Gln Arg Asn Tyr Leu Val Gln Thr Glu Glu Gln Tyr Ile Phe Ile His
225                 230                 235                 240
Asp Ala Leu Leu Glu
                245
```

(2) INFORMATION FOR SEQ ID NO:9:

(i) SEQUENCE CHARACTERISTICS:
        (A) LENGTH: 248 amino acids
        (B) TYPE: amino acid
        (C) STRANDEDNESS: single
        (D) TOPOLOGY: unknown (ii) MOLECULE TYPE: protein (ix) FEATURE:
        (A) NAME/KEY: Modified-sites
        (B) LOCATION: 1..248
        (D) OTHER INFORMATION: /label= Xaa
            /note= "For the Consensus Sequence, Xaa = Lack of -continued Consensus"

(xi) SEQUENCE DESCRIPTION: SEQ ID NO:9:

```
Asn Lys His Lys Asn Arg Tyr Xaa Asn Ile Leu Xaa Tyr Asp His Ser
1               5                   10                  15

Arg Val Lys Leu Xaa Xaa Leu Xaa Xaa Lys Xaa Xaa Lys Xaa Ser Asp
                20                  25                  30

Tyr Ile Asn Ala Xaa Tyr Xaa Asp Gly Tyr Asn Glu Pro Lys Xaa Tyr
            35                  40                  45

Ile Ala Ala Gln Gly Pro Leu Lys Xaa Thr Val Glu Asp Phe Trp Arg
50                      55                  60

Met Ile Trp Glu Gln Asn Thr Xaa Val Ile Val Met Xaa Thr Asn Leu
65                  70                  75                  80

Val Glu Lys Gly Arg Arg Lys Cys Xaa Gln Tyr Trp Pro Xaa Xaa Gly
                85                  90                  95

Ser Glu Xaa Tyr Gly Asn Ile Xaa Val Thr Val Lys Xaa Val Xaa Val
            100                 105                 110

Leu Ala Xaa Xaa Asp Tyr Thr Val Arg Lys Phe Xaa Xaa Arg Asn Thr
            115                 120                 125

Lys Ile Xaa Lys Xaa Gly Xaa Lys Xaa Xaa Xaa Lys Gly Arg Xaa Xaa
130                 135                 140

Gly Arg Val Val Thr Gln Tyr His Xaa Thr Xaa Trp Pro Asp Met Gly
145                 150                 155                 160

Val Pro Glu Tyr Pro Leu Pro Val Leu Xaa Phe Val Arg Xaa Val Xaa
                165                 170                 175

Ala Ala Xaa Xaa Xaa Xaa Xaa Gly Pro Xaa Val Val His Cys Ser Ala
            180                 185                 190

Gly Val Gly Arg Thr Gly Thr Tyr Ile Val Ile Asp Xaa Met Leu Gln
            195                 200                 205

Gln Ile Xaa Xaa Glu Xaa Xaa Val Xaa Val Tyr Gly Phe Xaa Lys His
            210                 215                 220

Ile Arg Xaa Gln Arg Xaa Tyr Xaa Val Gln Thr Glu Glu Gln Tyr Xaa
225                 230                 235                 240

Phe Ile His Xaa Ala Leu Xaa Glu
                245
```

(2) INFORMATION FOR SEQ ID NO:10:

(i) SEQUENCE CHARACTERISTICS:
        (A) LENGTH: 260 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:10:

```
Asn Lys Ser Lys Asn Arg Asn Ser Asn Val Ile Pro Tyr Asp Tyr Asn
1               5                   10                  15

Arg Val Pro Leu Lys His Glu Leu Glu Met Ser Lys Glu Ser Glu His
                20                  25                  30

Asp Ser Asp Glu Ser Ser Asp Asp Ser Asp Ser Glu Glu Pro Ser
            35                  40                  45

Lys Tyr Ile Asn Ala Ser Phe Ile Met Ser Tyr Trp Lys Pro Glu Val
        50                  55                  60

Met Ile Ala Ala Gln Gly Pro Leu Lys Glu Thr Ile Gly Asp Phe Trp
65                  70                  75                  80
```

```
Gln Met Ile Phe Gln Arg Lys Val Lys Val Ile Val Met Leu Thr Glu
                85                  90                  95
Leu Lys His Gly Asp Gln Glu Ile Cys Ala Gln Tyr Trp Gly Glu Gly
            100                 105                 110
Lys Gln Thr Tyr Gly Asp Ile Glu Val Asp Leu Lys Asp Thr Asp Lys
            115                 120                 125
Ser Ser Thr Tyr Thr Leu Arg Val Phe Glu Leu Arg His Ser Lys Arg
    130                 135                 140
Lys Asp Ser Arg Thr Val Tyr Gln Tyr Gln Tyr Thr Asn Trp Ser Val
145                 150                 155                 160
Glu Gln Leu Pro Ala Glu Pro Lys Glu Leu Ile Ser Met Ile Gln Val
                165                 170                 175
Val Lys Gln Lys Leu Pro Gln Lys Asn Ser Ser Glu Gly Asn Lys His
            180                 185                 190
His Lys Ser Thr Pro Leu Leu Ile His Cys Arg Asp Gly Ser Gln Gln
            195                 200                 205
Thr Gly Ile Phe Cys Ala Leu Leu Asn Leu Leu Glu Ser Ala Glu Thr
    210                 215                 220
Glu Glu Val Val Asp Ile Phe Gln Val Lys Ala Leu Arg Lys Ala
225                 230                 235                 240
Arg Pro Gly Met Val Ser Thr Phe Glu Gln Tyr Gln Phe Leu Tyr Asp
                245                 250                 255
Val Ile Ala Ser
            260

(2) INFORMATION FOR SEQ ID NO:11:

(i) SEQUENCE CHARACTERISTICS:
        (A) LENGTH: 233 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:11:

Asn Met Lys Lys Asn Arg Val Leu Gln Ile Ile Pro Tyr Glu Phe Asn
1               5                   10                  15
Arg Val Ile Ile Pro Val Lys Arg Gly Glu Glu Asn Thr Asp Tyr Val
                20                  25                  30
Asn Ala Ser Phe Ile Asp Gly Tyr Arg Gln Lys Asp Ser Tyr Ile Ala
            35                  40                  45
Ser Gln Gly Pro Leu Leu His Thr Ile Glu Asp Phe Trp Arg Met Ile
    50                  55                  60
Trp Glu Trp Lys Ser Cys Ser Ile Val Met Leu Thr Glu Leu Glu Glu
65                  70                  75                  80
Arg Gly Gln Glu Lys Cys Ala Gln Tyr Trp Pro Ser Asp Gly Leu Val
                85                  90                  95
Ser Tyr Gly Asp Ile Thr Val Glu Leu Lys Lys Glu Glu Glu Cys Glu
            100                 105                 110
Ser Tyr Thr Val Arg Asp Leu Leu Val Thr Asn Thr Arg Glu Asn Lys
            115                 120                 125
Ser Arg Gln Ile Arg Gln Phe His Phe His Gly Trp Pro Glu Val Gly
    130                 135                 140
Ile Pro Ser Asp Gly Lys Gly Met Ile Ser Ile Ile Ala Ala Val Gln
145                 150                 155                 160
```

Lys Gln Gln Gln Gln Ser Gly Asn His Pro Ile Thr Val His Cys Ser
            165                 170                 175

Ala Gly Ala Gly Arg Thr Gly Thr Phe Cys Ala Leu Ser Thr Val Leu
            180                 185                 190

Glu Arg Val Lys Ala Glu Gly Ile Leu Asp Val Phe Gln Thr Val Lys
            195                 200                 205

Ser Leu Ala Leu Gln Arg Pro His Met Val Gln Thr Leu Glu Gln Tyr
            210                 215                 220

Glu Phe Cys Tyr Lys Val Val Gln Glu
225                 230

(2) INFORMATION FOR SEQ ID NO:12:

(i) SEQUENCE CHARACTERISTICS:
        (A) LENGTH: 234 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:12:

Asn Arg Glu Lys Asn Arg Thr Ser Ser Ile Ile Pro Val Glu Arg Ser
1               5                   10                  15

Arg Val Gly Ile Ser Ser Leu Ser Gly Glu Gly Thr Asp Tyr Ile Asn
            20                  25                  30

Ala Ser Tyr Ile Met Gly Tyr Tyr Gln Ser Asn Glu Phe Ile Ile Thr
            35                  40                  45

Gln His Pro Leu Leu His Thr Ile Lys Asp Phe Trp Arg Met Ile Trp
50                  55                  60

Asp His Asn Ala Gln Leu Val Val Met Ile Pro Asp Gly Gln Asn Met
65                  70                  75                  80

Ala Glu Asp Glu Phe Val Tyr Trp Pro Asn Lys Asp Glu Pro Ile Asn
            85                  90                  95

Cys Glu Ser Phe Lys Val Thr Leu Met Ala Glu Glu His Lys Cys Leu
            100                 105                 110

Ser Asn Glu Glu Lys Leu Ile Ile Gln Asp Phe Ile Leu Glu Ala Thr
            115                 120                 125

Gln Asp Asp Tyr Val Leu Glu Val Arg His Phe Gln Cys Pro Lys Trp
130                 135                 140

Pro Asn Pro Asp Ser Pro Ile Ser Lys Thr Phe Glu Leu Ile Ser Val
145                 150                 155                 160

Ile Lys Glu Glu Ala Ala Asn Arg Asp Gly Pro Met Ile Val His Asp
            165                 170                 175

Glu His Gly Gly Val Thr Ala Gly Thr Phe Cys Ala Leu Thr Thr Leu
            180                 185                 190

Met His Gln Leu Glu Lys Glu Asn Ser Val Asp Val Tyr Gln Val Ala
            195                 200                 205

Lys Met Ile Asn Leu Met Arg Pro Gly Val Phe Ala Asp Ile Glu Gln
            210                 215                 220

Tyr Gln Phe Leu Tyr Lys Val Ile Leu Ser
225                 230

(2) INFORMATION FOR SEQ ID NO:13:

(i) SEQUENCE CHARACTERISTICS:
        (A) LENGTH: 235 amino acids (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:13:

Asn Lys Glu Lys Asn Arg Asn Ser Ser Val Val Pro Ser Glu Arg Ala
1               5                   10                  15

Arg Val Gly Leu Ala Pro Leu Pro Gly Met Lys Gly Thr Asp Tyr Ile
            20                  25                  30

Asn Ala Ser Tyr Ile Met Gly Tyr Tyr Arg Ser Asn Glu Phe Ile Ile
                35                  40                  45

Thr Gln His Pro Leu Pro His Thr Thr Lys Asp Phe Trp Arg Met Ile
        50                  55                  60

Trp Asp His Asn Ala Gln Ile Ile Val Met Leu Pro Asp Asn Gln Ser
65                  70                  75                  80

Leu Ala Glu Asp Glu Phe Val Tyr Trp Pro Ser Arg Glu Glu Ser Met
                85                  90                  95

Asn Cys Glu Ala Phe Thr Val Thr Leu Ile Ser Lys Asp Arg Leu Cys
            100                 105                 110

Leu Ser Asn Glu Glu Gln Ile Ile Ile His Asp Phe Ile Leu Glu Ala
        115                 120                 125

Thr Gln Asp Asp Tyr Val Leu Glu Val Arg His Phe Gln Cys Pro Lys
    130                 135                 140

Trp Pro Asn Pro Asp Ala Pro Ile Ser Ser Thr Phe Glu Leu Ile Asn
145                 150                 155                 160

Val Ile Lys Glu Glu Ala Leu Thr Arg Asp Gly Pro Thr Ile Val His
                165                 170                 175

Asp Glu Tyr Gly Ala Val Ser Ala Gly Met Leu Cys Ala Leu Thr Thr
            180                 185                 190

Leu Ser Gln Gln Leu Glu Asn Glu Asn Ala Val Asp Val Phe Gln Val
        195                 200                 205

Ala Lys Met Ile Asn Leu Met Arg Pro Gly Val Phe Thr Asp Ile Glu
    210                 215                 220

Gln Tyr Gln Phe Ile Tyr Lys Ala Arg Leu Ser
225                 230                 235

(2) INFORMATION FOR SEQ ID NO:14:

(i) SEQUENCE CHARACTERISTICS:
        (A) LENGTH: 280 amino acids
        (B) TYPE: amino acid
        (C) STRANDEDNESS: single
        (D) TOPOLOGY: unknown (ii) MOLECULE TYPE: protein (ix) FEATURE:
        (A) NAME/KEY: Modified-sites
        (B) LOCATION: 1..280
        (D) OTHER INFORMATION: /label= Xaa
            /note= "For the Consensus Sequence, Xaa = Lack of
            Consensus"

(xi) SEQUENCE DESCRIPTION: SEQ ID NO:14:

Asn Lys Glu Lys Asn Arg Asn Ser Ser Xaa Ile Pro Tyr Glu Arg Asn
1               5                   10                  15

Arg Val Gly Xaa Xaa Xaa Leu Xaa Xaa Xaa Xaa Xaa Xaa Xaa Xaa Xaa
            20                  25                  30

```
Xaa Xaa Xaa Xaa Xaa Xaa Xaa Xaa Xaa Xaa Xaa Gly Glu Glu Gly Thr
            35                  40                  45

Asp Tyr Ile Asn Ala Ser Xaa Ile Met Gly Tyr Tyr Gln Ser Asn Glu
        50                  55                  60

Phe Ile Xaa Thr Gln Xaa Pro Leu Leu His Thr Ile Lys Asp Phe Trp
65                  70                  75                  80

Arg Met Ile Trp Asp His Xaa Asn Ala Gln Ile Val Met Leu Xaa Xaa
            85                  90                  95

Xaa Gln Xaa Xaa Ala Glu Xaa Glu Xaa Xaa Gln Tyr Trp Pro Ser Xaa
            100                 105                 110

Gly Xaa Xaa Xaa Tyr Gly Asp Xaa Xaa Val Xaa Leu Lys Xaa Xaa Xaa
            115                 120                 125

Asn Cys Glu Ser Xaa Thr Val Thr Xaa Xaa Xaa Glu Xaa Arg Xaa Cys
            130                 135                 140

Leu Ser Asn Glu Xaa Arg Xaa Ile Ile Gln Asp Phe Ile Leu Glu Ala
145                 150                 155                 160

Thr Gln Asp Asp Tyr Val Leu Glu Val Arg His Phe Gln Cys Pro Lys
            165                 170                 175

Trp Pro Asn Pro Asp Xaa Pro Ile Ser Xaa Thr Xaa Glu Leu Ile Ser
            180                 185                 190

Val Ile Xaa Xaa Xaa Xaa Xaa Xaa Xaa Xaa Gln Lys Xaa Glu Glu Ala
            195                 200                 205

Xaa Asn Arg Xaa Xaa Xaa Asp Gly Pro Xaa Ile Val His Xaa Glu Xaa
            210                 215                 220

Gly Ala Val Xaa Xaa Gly Thr Phe Cys Ala Leu Thr Thr Leu Leu Glu
225                 230                 235                 240

Gln Leu Glu Xaa Glu Asn Xaa Val Asp Val Phe Gln Val Xaa Lys Met
            245                 250                 255

Xaa Asn Leu Met Arg Pro Gly Xaa Xaa Xaa Xaa Ile Glu Gln Tyr Gln
            260                 265                 270

Phe Leu Tyr Lys Val Ile Leu Ser
            275                 280
```